US006255095B1

(12) United States Patent
Prescott et al.

(10) Patent No.: US 6,255,095 B1
(45) Date of Patent: Jul. 3, 2001

(54) HUMAN DIACYLGLYCEROL KINASE IOTA

(75) Inventors: Stephen M. Prescott, Austin, TX (US); Li Ding, Palo Alto, CA (US); Elie Traer, Dallas, TX (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/412,545

(22) Filed: Oct. 5, 1999

Related U.S. Application Data

(60) Provisional application No. 60/103,079, filed on Oct. 5, 1998.

(51) Int. Cl.[7] ............................... C12N 9/12; C12N 1/20; C12N 15/00; C07H 21/04; C07K 1/00

(52) U.S. Cl. ...................... 435/194; 435/325; 435/252.3; 435/320.1; 536/23.2; 536/23.5; 530/350

(58) Field of Search ..................................... 435/194, 325, 435/252.3, 320.1; 536/23.2, 23.5; 530/350

(56) References Cited

U.S. PATENT DOCUMENTS 5,976,875 * 11/1999 Prescott et al. ...................... 435/325

OTHER PUBLICATIONS

Ding et al., "The Cloning and Characterization of a Novel Human Diacylglycerol Kinase, DGKI"; Journal of Biological Chemistry; vol. 273; pp. 32746–32752, 1998.

Masai et al., "DROSOPHILA Retinal Degeneration A Gene Encodes an Eye–Specific Diacylglycerol Kinase with Cysteine–Rich Zinc–Finger MOTIFS and Ankyrin Repeats"; Proc. Natl. Acad.; vol. 90; pp. 11157–11161, 1993.

* cited by examiner

*Primary Examiner*—Tekchand Saidha
(74) *Attorney, Agent, or Firm*—Madson & Metcalf

(57) ABSTRACT

Diacylglycerol (DAG) plays a central role in both the synthesis of complex lipids and in intracellular signaling; diacylglycerol kinase (DGK) catalyzes the phosphorylation of DAG, which yields phosphatidic acid. A family of DGKs has been identified in multicellular organisms over the past few years, but the physiological function(s) of this diversity is not clear. One clue has come from the Drosophila DGK2, rdgA, since mutations in this gene cause retinal degeneration. The present invention relates to a novel DGK, designated DGKι, which was isolated from human retina and brain libraries. DGKι contains two cysteine-rich repeats, a region similar to the phosphorylation site domain of MARCKS, a conserved catalytic domain, and four ankyrin repeats at its C-terminus. By primary structure, DGKι is most similar to human DGKζ and Drosophila rdgA. A>12 kb mRNA for DGKι was detected only in brain and retina among the tissues examined. In cells transfected with the DGKι cDNA, an approximately 130 kDa protein was detected by immunoassay, and activity assays demonstrated that it encodes a functional DAG kinase. The protein was found to be in both the cytoplasm and nucleus, with this localization controlled by PKC isoforms α and γ. The gene encoding DGKι was localized to human chromosome 7q32.3-33, which is known to be a locus for an inherited form of retinitis pigmentosa. These results have defined a novel isoform of DAG kinase, which may have important cellular functions in the retina and brain.

15 Claims, 17 Drawing Sheets

(1 of 17 Drawing Sheet(s) Filed in Color)

```
GGGACCATCCTGGCTAACACGCGGTAAACATCATCTCTACTAAAAAAATTA      60
GCCAGGCGTGGTAGCAGGCACCTGTGTCCCAGCTACTCGGGAGGCTGAGGCAGGAGAAT  120
GGGCGTGAACCCAGGAGGCGGAGCGGAGCTGCAGTGAGCTGAGATCACACCACTGCAATCCAGCC 180
TGGGCGACAAAGCAAGACTCTGTCTCAAAAAAAATCAACTCAGGAGGCCAAGTGTGGTG  240
GTGCACACCTGTAGTCCCAGCTACTGGGAAAGCTGAAGAAGTGGGAGGATAGCTTGGGCC  300
CAGGAGATGATGCTGCGGAAGGGCTGCCATTGCTGCCCCTGCCAGCGGCGCGGGA      360
           M  D  A  A  G  R  G  C  H  L  L  P  L  P  A  A  R  G
CCTGCCCGCGCTCCTGCAGCCGCGCGCCGCCGCCGCCGCGCCCGGCCCCCTGCAGC      420
 P  A  R  A  P  A  A  A  A  A  A  A  A  S  P  P  G  P  C  S
GGCGCCGCCTGCGCTCCCCGCTCCCCAGCTCCTCG                           480
 G  A  A  C  A  P  S  A  A  A  G  A  M  N  P  S  S  S
GCGGGAGGAGAAAGGGGCGACGGGCAGCAGCAGCAGCGGCGAAGCGGCGCGGGAGC      540
 A  G  E  E  K  G  A  T  G  G  S  S  S  S  G  S  G  A  G  S
TGCTGCCTGGGCGCGAGGGCGGGGCGGACCCGCGCGGGGTCAGCGCGGCG            600
 C  C  L  G  A  E  G  G  A  D  P  R  G  A  G  S  A  A  A  A
GGGGCCGCTGCCCTGGACGAGCCCGCGGCCGCCGCCGGGCAGAAGGAGAAGGACGAAGCGCTG  660
 G  A  A  A  L  D  E  P  A  A  A  A  G  Q  K  E  K  D  E  A  L
```

FIG. 1b-1

```
CAGGAGGGGAAATGTAAGCAGTGTGGTAAGGGCTTCCAGCAAAAGTTCTCCTTCCACAGT  1140
 Q  E  G  K  C  K  Q  C  G  K  G  F  Q  Q  K  F  S  F  H  S

AAAGAGATTGTGGCTATCAGCTGTGTCCTGGTGCAAGCAGGCGTTCACAATAAGGTGACC  1200
 K  E  I  V  A  I  S  C  V  L  V  Q  A  G  V  H  N  K  V  T

TGCTTCATGCTGCATCACATTGAAGAACCCTGCTCCCTGGGGGCTCATGCTGCTGTTATT  1260
 C  F  M  L  H  H  I  E  E  P  C  S  L  G  A  H  A  A  V  I

GTCCCGCCCACTTGGATCATTAAGGTGAAGAAACCTCAGAACTCCCTGAAGGCTTCAAAT  1320
 V  P  P  T  W  I  I  K  V  K  K  P  Q  N  S  L  K  A  S  N

CGGAAGAAGAAGAGAACAAGCTTTAAAAGAAAAGCCAGTAAAAGAGGGATGGAACAGGAA  1380
 R  K  K  K  R  T  S  F  K  R  K  A  S  K  R  G  M  E  Q  E

AACAAAGGTCGTCCTTTTGTGATAAAACCCATCTCTTCTCCTCTCATGAAACCCTTGCTT  1440
 N  K  G  R  P  F  V  I  K  P  I  S  S  P  L  M  K  P  L  L
```

FIG. 1b-3

```
GTATTTGTGAATCCCAAGAGTGGAGGCAACCAGGAACCAAAGTCCTGCAGATGTTCATG  1500
 V  F  V  N  P  K  S  G  G  N  Q  G  T  K  V  L  Q  M  F  M

TGGTACCTGAATCCACGGCAAGTCTTTGATCTTTTCAGGAAGGCCAAAAGATGCGCTT  1560
 W  Y  L  N  P  R  Q  V  F  D  L  S  Q  E  G  P  K  D  A  L

GAATTGTATAGGAAAGTACCAAATCTGCGAATTCTGGCTTGTGGGATGGAACGGTG  1620
 E  L  Y  R  K  V  P  N  L  R  I  L  A  C  G  G  D  G  T  V

GGCTGGATCCTTCCATCCTGGATGAACTGCAGCTGAGCCCCTCCAGCCTGTGGGGTC  1680
 G  W  I  L  S  I  L  D  E  L  Q  L  S  P  Q  P  P  V  G  V

CTTCCCTCTGGGGACTGGGAATGACCTGGCTCGAACTCTCAACTGGGAGGGGCTACACT  1740
 L  P  L  G  T  G  N  D  L  A  R  T  L  N  W  G  G  Y  T

GATGAACCTGTTTCTAAGATCCTGTGTCAAGTGGAAGATGGACAGTGTACAGCTAGAT  1800
 D  E  P  V  S  K  I  L  C  Q  V  E  D  G  T  V  V  Q  L  D

CGCTGGAACCTCCATGTGGAAAGAAACCCCGACTTGCCTCCAGAAGAACTTGAAGATGGC  1860
 R  W  N  L  H  V  E  R  N  P  D  L  P  P  E  E  L  E  D  G
```

FIG. 1b-4

```
GTATGTAAGCTCCCTCTGAATGTTTCAATAACTACTTCAGCCTTGGATTTGATGCCCAT  1920
 V  C  K  L  P  L  N  V  F  N  N  Y  F  S  L  G  F  D  A  H

GTCACACTGGAGTTCCATGAATCCAGAGAAGCAAATTCAACAGTCGTTTT  1980
 V  T  L  E  F  H  E  S  R  E  A  N  P  E  K  E  F  N  S  R  F

CGAAATAAAATGTTCTATGCAGGGGCAGCTTTTTCTGACTTCCTACAGAGAAGTTCTAGA  2040
 R  N  K  M  F  Y  A  G  A  A  F  S  D  F  L  Q  R  S  S  R

GATCTATCCAAACATGTTAAAGTTGTTTGTGATGGAACAGATCTCACCCCAAAGATTCAG  2100
 D  L  S  K  H  V  K  V  V  C  D  G  T  D  L  T  P  K  I  Q

GAACTGAAGTTCCAGTGTATAGTATTTTTAAATATACCCAGATATTGTGCTGGCACAATG  2160
 E  L  K  F  Q  C  I  V  F  L  N  I  P  R  Y  C  A  G  T  M
```

FIG. 1b-5

```
CCCTGGGGAAACCCAGTGATCACCATGATTTCGAACCTCAGCGTCATGATGGTTAT  2220
 P  W  G  N  P  G  D  H  H  D  F  E  P  Q  R  H  D  D  G  Y

ATTGAAGTCATTGGATTTACCATGGCCTCTTTGGCAGCCCTGCAAGTTGGGGCCATGGA  2280
 I  E  V  I  G  F  T  M  A  S  L  A  A  L  Q  V  G  G  H  G

GAGAGGCTACACCAGTGTCGAGAAGTCATGCTTCTAACTTACAAATCCATCCCCATGCAA  2340
 E  R  L  H  Q  C  R  E  V  M  L  L  T  Y  K  S  I  P  M  Q

GTGGATGGGGAGCCCTGTAGGTTGGCCCCAGCTATGATTCGGATCTCCCTGAGGAATCAG  2400
 V  D  G  E  P  C  R  L  A  P  A  M  I  R  I  S  L  R  N  Q

GCCAACATGGTACAGAAGAGCAAGAGGAGAACATCCATGCCTTTACTCAATGATCCCCAG  2460
 A  N  M  V  Q  K  S  K  R  R  T  S  M  P  L  L  N  D  P  Q

TCTGTCCCAGATCGTCTGAGGATCCGGGTGAACAAAATCAGTTTACAAGACTATGAAGGA  2520
 S  V  P  D  R  L  R  I  R  V  N  K  I  S  L  Q  D  Y  E  G

TTCCACTATGACAAGGAGAAACTCCGAGAAGCTTCTATTTCAGACTGGTTAAGAACCATT  2580
 F  H  Y  D  K  E  K  L  R  E  A  S  I  S  D  W  L  R  T  I
```

FIG. 1b-6

```
GCTGGGGAACTAGTGCAGTCATTTGGAGCGATACCCTCTGGGTATTCTAGTTGTGCCGTGGA  2640
 A  G  E  L  V  Q  S  F  G  A  I  P  L  G  I  L  V  V  R  G

GACTGTGATTTGGAGACTTGCCGTATGTACATAGACCGCCTACAGGAGGACCTACAGTCA    2700
 D  C  D  L  E  T  C  R  M  Y  I  D  R  L  Q  E  D  L  Q  S

GTTTCTTCTGGCTCCCAGAGAGTTCATTACCAGGACCATGAAACCTCCTTCCCCAGGGCT    2760
 V  S  S  G  S  Q  R  V  H  Y  Q  D  H  E  T  S  F  P  R  A

CTCTCAGCACAGAGGCTCTCCTCCTCGGTGGTGCTTCCTAGATGACAGATCTCAGGAACAT   2820
 L  S  A  Q  R  L  S  P  R  W  C  F  L  D  D  R  S  Q  E  H

TTGCACTTTGTGATGGAGATTTCCCAAGATGAGATTTTTATTCTGGACCCAGATATGGTG    2880
 L  H  F  V  M  E  I  S  Q  D  E  I  F  I  L  D  P  D  M  V

GTGTCACAGCCGGGGACACCTCCGGGCATGCCTGGTGGTGGAACAAGCCTCG            2940
 V  S  Q  P  P  A  G  T  P  P  G  M  P  D  L  V  V  E  Q  A  S

GGGATCTCAGACTGGTGGAATCCTGCCCTGCGGAAACGCATGCTGAGTGACAGTGGGCTG    3000
 G  I  S  D  W  W  N  P  A  L  R  K  R  M  L  S  D  S  G  L

FIG. 1b-7
```

```
GGGATGATAGCTCCCTATTATGAGGACTCGAAAGATCTCAGCCACTCCCGCGTG  3060
 G  M  I  A  P  Y  Y  E  D  S  D  L  K  D  L  S  H  S  R  V
CTACAGTCACCAGTCTCTTCAGAAGATCATGCAATTTGCAGGCAGTAATAGCTGGTGAT  3120
 L  Q  S  P  V  S  E  D  H  A  I  L  Q  A  V  I  A  G  D
CTTATGAAGCTAATAGAAAGCTATAAAAATGGAGGCAGTCTGCTAATTCAGGGACCAGAC  3180
 L  M  K  L  I  E  S  Y  K  N  G  G  S  L  L  I  Q  G  P  D
CACTGTTCACTCCTTCACTACGCCAGCTAAAACCGGCAACGGGGAGATTGTGAAATATATC  3240
 H  C  S  L  H  Y  A  A  K  T  G  N  G  E  I  V  K  Y  I
CTTGACCACGGACCTTCCGAGTTATTGGATATGGCAGACAGTGAAACGGGTGAGACTGCA  3300
 L  D  H  G  P  S  E  L  L  D  M  A  D  S  E  T  G  E  T  A
CTGCACAAGGCTGCCTGCCAGCGGAACCGGGTGTGCCAGCTTCTGGTGGATGCAGGA  3360
 L  H  K  A  A  C  Q  R  N  R  A  V  C  Q  L  L  V  D  A  G
GCATCTCTGAGAAAGACGGACTCCAAGGTAAGACACCTCAAGAAAGAGCACAGCCAGGCT  3420
 A  S  L  R  K  T  D  S  K  G  K  T  P  Q  E  R  A  Q  Q  A
```

FIG. 1b-8

GGGGACCCCAGACTTGGCTGCTTACCTAGAAAGCCCGTCAGAACTATAAGGTCATTGGCCAT 3480
 G  D  P  D  L  A  A  Y  L  E  S  R  Q  N  Y  K  V  I  G  H

GAGGACCTGGAAACTGCTGTTTGACCCTGGTATTCGGGCAAAGAGGACATGAGCAAGCGT 3540
 E  D  L  E  T  A  V

FIG. 1b-9

```
ATCACATCTGCCCTCCCTGCAATTGGGCAGCTCCCCTGGAAGAAGCTGATGGAATTCATA  3600
TATCTGTCTCTCCTGCAAGAATCTACCTGAGACCATGCCACTAGCTTTAAGGGCTAC    3660
CAAGATGTACAACAGAACATGATAGCCCATTGAGAAGGAGGCAGGATACCTGGAGATTTG  3720
TGGAATACAGTACGAGTTCCACAAATTGATCCTTATTGCTTCCAGCAAGTAGCATGAA    3780
CTTCTGTGTTCACCTGTATAATTTATTTAAAGATTCAAAGGATGTTCGTATAAATGGCA  3840
CTGCTCCATCCTCCCCCTATGCATTGGTTTTTTCCCTGTACCATACAATTCTACTGTAA  3900
CTACCCATCAACTTAAAGAAAAATATTATCTCTTCTTTACATTCAGTCTTGAAGACC    3960
ACAAGATTGTCTGAAGGCCTTCTAAGACTAAATATCAAGACTATTTAGTGACTCTCTGCATGT  4020
AACCACTTCCATTTCTAAGACTAAATATCAAGACTATTTAGTGACTCTCTGCATGT    4080
CCCCCTCACCCGCCAACCCTCCGTTTCATTATATAGAGCTGGGAAGTGCCACATGGATA  4140
ATGTCAACTTGTGTGCTATATCTCGAGGAATGGTGAGGTGAGTGGCATGGGAGATGTCTGTGC  4200
TTGGAGTACCTCAGAGAGTAACCCAGGGTCAGCAGCCAGGGTCTGTCTGTACAGCTCCGTACTGTGTAG  4260
AGCCATGCAGGACTGGTTCAGCTGGTCAATAGAAGATGAGCACTCTGTTTAAGTGCTGTTTAAATGCTGTT  4320
CCATCTTTGCCTTTGCAGAACCACTCAATTTAAGTGCTGTTTAAATGCTGTT    4380
AGTTTGCAGAACCACTCAATTTAAGTGCTGTTTAAATGCTGTTTACTTCTAAACTTGTGT  4440
GGGAACTGTGGTTACAGAAAGCACCCTAATTGACTTGGAAATAGGAAACAGTCATTGGAATGTTGCACAGAGC  4500
ATGATAATAGAAAGCACCCTAATTGACTTGGAAATAGGAAACAGTCATTGGAATGTTGCACAGAGC  4560
AACATATGTCAACATATGTCACTGAAATGTCACTGAAATAGGAAACAGTCATTGGAATGTTGCACAGAGC  4620
TAATAGCTATGGACTGTTGGATACAGATACAGTGGTGAGAGGAGCCCCATTTTAGGTCT  4680
TTCTTTTAGGTTTGGTTTTCATTACTCCAAGTAGCCCTTGACCCAAGAACAAAGGCTT  4740
GTTGTATGAGTTCCACTGCCAGTCCAGATTTATGGGATGCCTGGATCATTCAGAAGGATGCTTCA  4800
ACTATTATTGTCAGGTCCAAAGGTCGTACTTGATAACCCCATTTTCTATGTATGGGTA  4860
GTCTAATAATTATTTATCTACTTATTTTTCCCTTTTCAGAAAGTCCTTAGTCAAAC    4920
CACCATTGGAATCTAGTACAGAAATGTCTGTCAGATAGTTAGAATTGTAACATCTAAACCT  4980
GCCACGGATCGAATGACTACTTACAGTACCTCTCTTAGGGACTCCTGATCCCTAAAATA  5040
TCAGAAGAAAATGTCTGTCTTTCTGTCCAAATATCTACTTGACTTGGGGGTA
```

FIG. 1b-10

```
Ankyrin Repeat
Consensus Sequence  -G-TLPH-AA---GH----V---LL--GA---N----
                                      A         D hDGK1 repeat 1      ------AV---G----L------G------------
hDGK1 repeat 2      ---L-H-AA---G----V---IL---G---------
hDGK1 repeat 3      -G-T-LH-AA--------------LV---G------
hDGK1 repeat 4      -G-TP----A----G----A---L------------
```

FIG. 1c

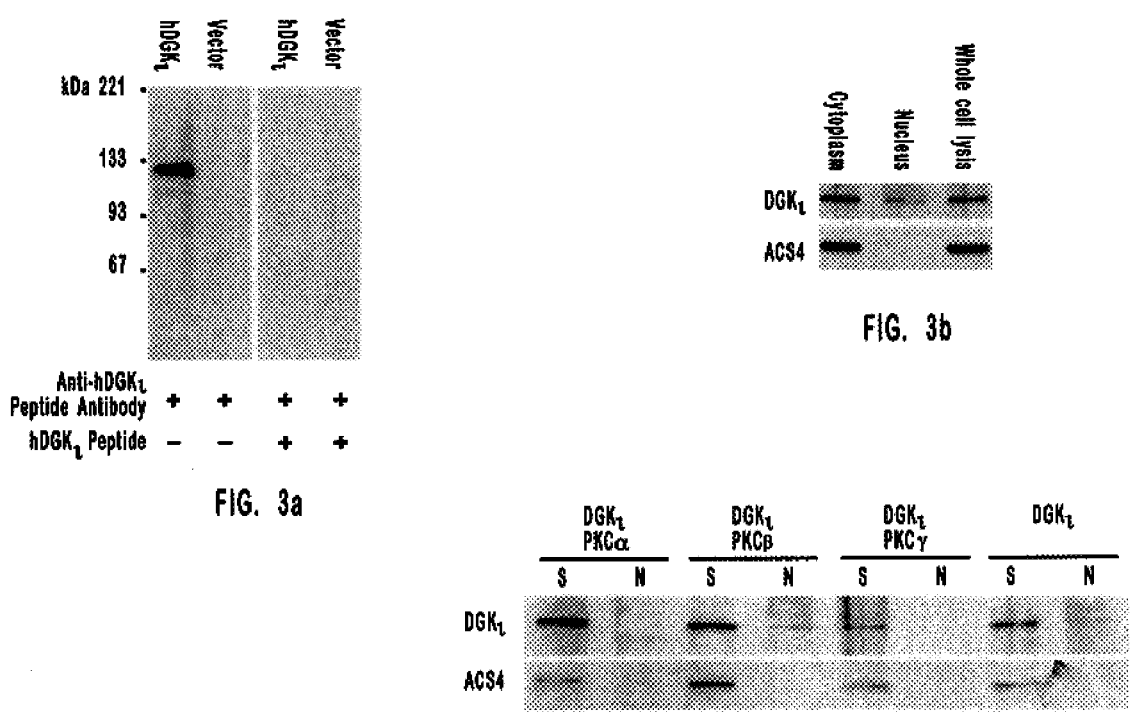

SEQUENCE LISTING

<160> NUMBER OF SEQ ID NOS: 8

<210> SEQ ID NO 1
<211> LENGTH: 5092
<212> TYPE: DNA
<213> ORGANISM: Homo sapiens
<220> FEATURE:
<221> NAME/KEY: CDS
<222> LOCATION: (307)..(3504)

<400> SEQUENCE: 1

```
gggaccatcc tggctaacac gcggtaaaac atcatctcta ctaaaaatac aaaaaaatta      60
gccaggcgtg gtagcaggca cctgttgtcc cagctactcg ggaggctgag gcaggagaat     120
ggcgtgaacc caggaggcgg agctggcagt gagctgagat cacaccactg caatccagcc     180
tgggcgacaa agcaagactc tgtctcaaaa aaaaaaaatc aattcaggcc aagtgtggtg     240
gtgcacacct gtagtcccag ctactgggaa agctgaagaa gtgggaggat agcttgggcc     300 caggag atg gat gct gcg gga agg ggc tgc cat ttg ctg ccc ctg cca         348
       Met Asp Ala Ala Gly Arg Gly Cys His Leu Leu Pro Leu Pro
         1               5                  10 gcg gcg cgc gga cct gcc cgc gct cct gca gcc gcc gcc gcc gcc gcc         396
Ala Ala Arg Gly Pro Ala Arg Ala Pro Ala Ala Ala Ala Ala Ala Ala
 15                  20                  25                  30 gcc agc ccg ccc ggc ccc tgc agc ggc gcc gcc tgc gct ccc tcc gcg         444
Ala Ser Pro Pro Gly Pro Cys Ser Gly Ala Ala Cys Ala Pro Ser Ala
                 35                  40                  45 gcc gcc gga gcg ggc gcc atg aac ccc agc tcc tcg gcg gga gag gag         492
Ala Ala Gly Ala Gly Ala Met Asn Pro Ser Ser Ser Ala Gly Glu Glu
             50                  55                  60 aaa ggg gcg acg ggc ggc agc agc agc gga agc ggc gcc ggg agc              540
Lys Gly Ala Thr Gly Gly Ser Ser Ser Gly Ser Gly Ala Gly Ser
 65                  70                  75 tgc tgc ctg ggc gcc gag ggc ggc gcg gac ccg cgg ggc gca ggg tca         588
Cys Cys Leu Gly Ala Glu Gly Gly Ala Asp Pro Arg Gly Ala Gly Ser
 80                  85                  90 gcc gcg gcg gcg ggg gcc gct gcc ctg gac gag ccc gcg gcc gcc ggc         636
Ala Ala Ala Ala Gly Ala Ala Ala Leu Asp Glu Pro Ala Ala Ala Gly
 95                 100                 105                 110 cag aag gag aag gac gaa gcg ctg gag gag aag ctg agg aac tta act         684
Gln Lys Glu Lys Asp Glu Ala Leu Glu Glu Lys Leu Arg Asn Leu Thr
                115                 120                 125 ttc cgg aag cag gtc tcg tac agg aaa gca atc tcc cgg gca ggc ctc         732
Phe Arg Lys Gln Val Ser Tyr Arg Lys Ala Ile Ser Arg Ala Gly Leu
            130                 135                 140 cag cat ctg gct cct gca cat ccc ctc agc ctt cct gtg gca aat ggt         780
Gln His Leu Ala Pro Ala His Pro Leu Ser Leu Pro Val Ala Asn Gly
        145                 150                 155 cca gcc aag gag ccc aga gcg act ttg gac tgg agt gag aat gcc gtg         828
Pro Ala Lys Glu Pro Arg Ala Thr Leu Asp Trp Ser Glu Asn Ala Val
    160                 165                 170
```

-continued

| | | |
|---|---|---|
| aat gga gaa cac ctg tgg ctg gag acc aac gtc tcg gga gac ctc tgc<br>Asn Gly Glu His Leu Trp Leu Glu Thr Asn Val Ser Gly Asp Leu Cys<br>175                        180                       185                     190 | 876 | |
| tac ctt gga gag gag aac tgc caa gtc aga ttt gca aaa tca gct ctc<br>Tyr Leu Gly Glu Glu Asn Cys Gln Val Arg Phe Ala Lys Ser Ala Leu<br>                       195                     200                     205 | 924 | |
| agg agg aag tgt gca gtc tgt aaa atc gtc gtc cac acc gcc tgc att<br>Arg Arg Lys Cys Ala Val Cys Lys Ile Val Val His Thr Ala Cys Ile<br>210                       215                    220 | 972 | |
| gag cag cta gaa aag att aat ttc aga tgt aaa cca aca ttt cga gaa<br>Glu Gln Leu Glu Lys Ile Asn Phe Arg Cys Lys Pro Thr Phe Arg Glu<br>        225                    230                    235 | 1020 | |
| gga ggc tca agg tca cca aga gaa aat ttt gta cgt cat cac tgg gtg<br>Gly Gly Ser Arg Ser Pro Arg Glu Asn Phe Val Arg His His Trp Val<br>240                       245                    250 | 1068 | |
| cac agg cgt cgg cag gag ggg aaa tgt aag cag tgt ggt aag ggc ttc<br>His Arg Arg Arg Gln Glu Gly Lys Cys Lys Gln Cys Gly Lys Gly Phe<br>255                       260                    265                    270 | 1116 | |
| cag caa aag ttc tcc ttc cac agt aaa gag att gtg gct atc agc tgt<br>Gln Gln Lys Phe Ser Phe His Ser Lys Glu Ile Val Ala Ile Ser Cys<br>               275                    280                    285 | 1164 | |
| tcc tgg tgc aag cag gcg ttt cac aat aag gtg acc tgc ttc atg ctg<br>Ser Trp Cys Lys Gln Ala Phe His Asn Lys Val Thr Cys Phe Met Leu<br>              290                    295                    300 | 1212 | |
| cat cac att gaa gaa ccc tgc tcc ctg ggg gct cat gct gct gtt att<br>His His Ile Glu Glu Pro Cys Ser Leu Gly Ala His Ala Ala Val Ile<br>                     305                    310                    315 | 1260 | |
| gtc ccg ccc act tgg atc att aag gtg aag aaa cct cag aac tcc ctg<br>Val Pro Pro Thr Trp Ile Ile Lys Val Lys Lys Pro Gln Asn Ser Leu<br>320                       325                    330 | 1308 | |
| aag gct tca aat cgg aag aag aag aga aca agc ttt aaa aga aaa gcc<br>Lys Ala Ser Asn Arg Lys Lys Lys Arg Thr Ser Phe Lys Arg Lys Ala<br>335                       340                    345                    350 | 1356 | |
| agt aaa aga ggg atg gaa cag gaa aac aaa ggt cgt cct ttt gtg ata<br>Ser Lys Arg Gly Met Glu Gln Glu Asn Lys Gly Arg Pro Phe Val Ile<br>                     355                    360                    365 | 1404 | |
| aaa ccc atc tct tct cct ctc atg aaa ccc ttg ctt gta ttt gtg aat<br>Lys Pro Ile Ser Ser Pro Leu Met Lys Pro Leu Leu Val Phe Val Asn<br>             370                    375                    380 | 1452 | |
| ccc aag agt gga ggc aac cag gga acc aaa gtc ctg cag atg ttc atg<br>Pro Lys Ser Gly Gly Asn Gln Gly Thr Lys Val Leu Gln Met Phe Met<br>385                       390                    395 | 1500 | |
| tgg tac ctg aat cca cgg caa gtc ttt gat ctt tct cag gaa ggg cca<br>Trp Tyr Leu Asn Pro Arg Gln Val Phe Asp Leu Ser Gln Glu Gly Pro<br>400                       405                    410 | 1548 | |
| aaa gat gcg ctt gaa ttg tat agg aaa gta cca aat ctg cga att ctg<br>Lys Asp Ala Leu Glu Leu Tyr Arg Lys Val Pro Asn Leu Arg Ile Leu<br>415                       420                    425                    430 | 1596 | |
| gcc tgt ggt ggg gat gga acg gtg ggc tgg atc ctt tcc atc ctg gat<br>Ala Cys Gly Gly Asp Gly Thr Val Gly Trp Ile Leu Ser Ile Leu Asp<br>                     435                    440                    445 | 1644 | |
| gaa ctg cag ctg agc cct cag cct cct gtg ggg gtc ctt cct ctg ggg<br>Glu Leu Gln Leu Ser Pro Gln Pro Pro Val Gly Val Leu Pro Leu Gly<br>             450                    455                    460 | 1692 | |
| act ggg aat gac ctg gct cga act ctc aac tgg gga ggg ggc tac act<br>Thr Gly Asn Asp Leu Ala Arg Thr Leu Asn Trp Gly Gly Gly Tyr Thr<br>465                       470                    475 | 1740 | |
| gat gaa cct gtt tct aag atc ctg tgt caa gtg gaa gat ggg aca gtt<br>Asp Glu Pro Val Ser Lys Ile Leu Cys Gln Val Glu Asp Gly Thr Val | 1788 | |

```
                480                485                490
gta cag cta gat cgc tgg aac ctc cat gtg gaa aga aac ccc gac ttg    1836
Val Gln Leu Asp Arg Trp Asn Leu His Val Glu Arg Asn Pro Asp Leu
495                 500                505                510 cct cca gaa gaa ctt gaa gat ggc gta tgt aag ctc cct ctg aat gtt    1884
Pro Pro Glu Glu Leu Glu Asp Gly Val Cys Lys Leu Pro Leu Asn Val
                515                520                525 ttc aat aac tac ttc agc ctt gga ttt gat gcc cat gtc aca ctg gag    1932
Phe Asn Asn Tyr Phe Ser Leu Gly Phe Asp Ala His Val Thr Leu Glu
            530                535                540 ttc cat gaa tcc aga gaa gca aat cca gag aaa ttc aac agt cgt ttt    1980
Phe His Glu Ser Arg Glu Ala Asn Pro Glu Lys Phe Asn Ser Arg Phe
        545                550                555 cga aat aaa atg ttc tat gca ggg gca gct ttt tct gac ttc cta cag    2028
Arg Asn Lys Met Phe Tyr Ala Gly Ala Ala Phe Ser Asp Phe Leu Gln
    560                565                570 aga agt tct aga gat cta tcc aaa cat gtt aaa gtt gtt tgt gat gga    2076
Arg Ser Ser Arg Asp Leu Ser Lys His Val Lys Val Val Cys Asp Gly
575                580                585                590 aca gat ctc acc cca aag att cag gaa ctg aag ttc cag tgt ata gta    2124
Thr Asp Leu Thr Pro Lys Ile Gln Glu Leu Lys Phe Gln Cys Ile Val
                595                600                605 ttt tta aat ata ccc aga tat tgt gct ggc aca atg ccc tgg gga aac    2172
Phe Leu Asn Ile Pro Arg Tyr Cys Ala Gly Thr Met Pro Trp Gly Asn
            610                615                620 cca ggt gat cac cat gat ttc gaa cct cag cgt cat gat gat ggt tat    2220
Pro Gly Asp His His Asp Phe Glu Pro Gln Arg His Asp Asp Gly Tyr
        625                630                635 att gaa gtc att gga ttt acc atg gcc tct ttg gca gcc ctg caa gtt    2268
Ile Glu Val Ile Gly Phe Thr Met Ala Ser Leu Ala Ala Leu Gln Val
    640                645                650 ggg ggc cat gga gag agg cta cac cag tgt cga gaa gtc atg ctt cta    2316
Gly Gly His Gly Glu Arg Leu His Gln Cys Arg Glu Val Met Leu Leu
655                660                665                670 act tac aaa tcc atc ccc atg caa gtg gat ggg gag ccc tgt agg ttg    2364
Thr Tyr Lys Ser Ile Pro Met Gln Val Asp Gly Glu Pro Cys Arg Leu
                675                680                685 gcc cca gct atg att cgg atc tcc ctg agg aat cag gcc aac atg gta    2412
Ala Pro Ala Met Ile Arg Ile Ser Leu Arg Asn Gln Ala Asn Met Val
            690                695                700 cag aag agc aag agg aga aca tcc atg cct tta ctc aat gat ccc cag    2460
Gln Lys Ser Lys Arg Arg Thr Ser Met Pro Leu Leu Asn Asp Pro Gln
        705                710                715 tct gtc cca gat cgt ctg agg atc cgg gtg aac aaa atc agt tta caa    2508
Ser Val Pro Asp Arg Leu Arg Ile Arg Val Asn Lys Ile Ser Leu Gln
    720                725                730 gac tat gaa gga ttc cac tat gac aag gag aaa ctc cga gaa gct tct    2556
Asp Tyr Glu Gly Phe His Tyr Asp Lys Glu Lys Leu Arg Glu Ala Ser
735                740                745                750 att tca gac tgg tta aga acc att gct ggg gaa cta gtg cag tca ttt    2604
Ile Ser Asp Trp Leu Arg Thr Ile Ala Gly Glu Leu Val Gln Ser Phe
                755                760                765 gga gcg ata cct ctg ggt att cta gtt gtg cgt gga gac tgt gat ttg    2652
Gly Ala Ile Pro Leu Gly Ile Leu Val Val Arg Gly Asp Cys Asp Leu
            770                775                780 gag act tgc cgt atg tac ata gac cgc cta cag gag gac cta cag tca    2700
Glu Thr Cys Arg Met Tyr Ile Asp Arg Leu Gln Glu Asp Leu Gln Ser
        785                790                795 gtt tct tct ggc tcc cag aga gtt cat tac cag gac cat gaa acc tcc    2748
```

```
Val Ser Ser Gly Ser Gln Arg Val His Tyr Gln Asp His Glu Thr Ser
    800                 805                 810 ttc ccc agg gct ctc tca gca cag agg ctc tct cct cgg tgg tgc ttc    2796
Phe Pro Arg Ala Leu Ser Ala Gln Arg Leu Ser Pro Arg Trp Cys Phe
815                 820                 825                 830 cta gat gac aga tct cag gaa cat ttg cac ttt gtg atg gag att tcc    2844
Leu Asp Asp Arg Ser Gln Glu His Leu His Phe Val Met Glu Ile Ser
                835                 840                 845 caa gat gag att ttt att ctg gac cca gat atg gtg gtg tca cag ccg    2892
Gln Asp Glu Ile Phe Ile Leu Asp Pro Asp Met Val Val Ser Gln Pro
            850                 855                 860 gcg ggg aca cct ccg ggc atg cct gac ctg gtg gtg gaa caa gcc tcg    2940
Ala Gly Thr Pro Pro Gly Met Pro Asp Leu Val Val Glu Gln Ala Ser
        865                 870                 875 ggg atc tca gac tgg tgg aat cct gcc ctg cgg aaa cgc atg ctg agt    2988
Gly Ile Ser Asp Trp Trp Asn Pro Ala Leu Arg Lys Arg Met Leu Ser
    880                 885                 890 gac agt ggg ctg ggg atg ata gct ccc tat tat gag gac tca gat ctg    3036
Asp Ser Gly Leu Gly Met Ile Ala Pro Tyr Tyr Glu Asp Ser Asp Leu
895                 900                 905                 910 aaa gat ctc agc cac tcc cgc gtg cta cag tca cca gtc tct tca gaa    3084
Lys Asp Leu Ser His Ser Arg Val Leu Gln Ser Pro Val Ser Ser Glu
                915                 920                 925 gat cat gca att ttg cag gca gta ata gct ggt gat ctt atg aag cta    3132
Asp His Ala Ile Leu Gln Ala Val Ile Ala Gly Asp Leu Met Lys Leu
            930                 935                 940 ata gaa agc tat aaa aat gga ggc agt ctg cta att cag gga cca gac    3180
Ile Glu Ser Tyr Lys Asn Gly Gly Ser Leu Leu Ile Gln Gly Pro Asp
        945                 950                 955 cac tgt tca ctc ctt cac tac gca gct aaa acc ggc aac ggg gag att    3228
His Cys Ser Leu Leu His Tyr Ala Ala Lys Thr Gly Asn Gly Glu Ile
    960                 965                 970 gtg aaa tat atc ctt gac cac gga cct tcc gag tta ttg gat atg gca    3276
Val Lys Tyr Ile Leu Asp His Gly Pro Ser Glu Leu Leu Asp Met Ala
975                 980                 985                 990 gac agt gaa acg ggt gag act gca ctg cac aag gct gcc tgc cag cgg    3324
Asp Ser Glu Thr Gly Glu Thr Ala Leu His Lys Ala Ala Cys Gln Arg
                995                 1000                1005 aac cgg gct gtg tgc cag ctt ctg gtg gat gca gga gca tct ctg aga    3372
Asn Arg Ala Val Cys Gln Leu Leu Val Asp Ala Gly Ala Ser Leu Arg
            1010                1015                1020 aag acg gac tcc aag ggt aag aca cct caa gaa aga gca cag cag gct    3420
Lys Thr Asp Ser Lys Gly Lys Thr Pro Gln Glu Arg Ala Gln Gln Ala
        1025                1030                1035 ggg gac cca gac ttg gct gct tac cta gaa agc cgt cag aac tat aag    3468
Gly Asp Pro Asp Leu Ala Ala Tyr Leu Glu Ser Arg Gln Asn Tyr Lys
    1040                1045                1050 gtc att ggc cat gag gac ctg gaa act gct gtt tga ccctggtatt         3514
Val Ile Gly His Glu Asp Leu Glu Thr Ala Val
1055                1060                1065 cgggcaaaga ggacatgagc aagcgtatca catctgccct ccctgcaatt gggcagctcc  3574
cctggaagaa gctgatggaa ttcatatatc tgtctctctc ctgcaagaat ctacctgaga  3634
ccatgccact agcttttaag ggctaccaag atgtacaaca gaacatgata gcccattgag  3694
aaggaggcag gatacctgga gatttgtgga atacagtacg agttccacaa aatttgatcc  3754
ttattgcttc cagcaagtag catgaacttc tgtgttcacc tgtataattt attttaaaga  3814
ttcaaaggat gttcgtataa atggcactgc tccatcctcc ccctatgcat ggttttttt   3874
```

-continued

```
ccctgtacca tacaattcta ctgtaactac ccatcaactt aaagaaaaat attatctctt    3934
ctctttacat tcagtcttgg aagaccacaa gattgtctga aggccttcta aaaccttctg    3994
aatgtcctgc agaaatataa ctgtaaaacc acttccattt ctaagactaa atatatcaag    4054
actatttagt gactctctct gcatgtcccc ctcacccgcc aaccctccgt ttcattatat    4114
aggagctggg aagtgccaca tggataatgt caacttgtgt gctatatctc tgaggaatgg    4174
tgaggtggca tgggagatgt ctgtgcttgg aggtacctca gagaggtaac ccagggtca     4234 gcccaggctg ctgggctgta gccaatagcc atgcaggact ggttcagctt gggctgtctg    4294
tacagctccg tactgcctat gtgtagccat ctttgccttt tgctgcaata aagatgagc     4354 aaaggattaa acagaggccc acagctagtt gcagaaccca ctcaattta agtgctgttt    4414 aaattgcaga gcaaataatc ctgtgtggga actgtggtta caggaaatgg agcactctaa    4474
caatgtttac ttctaaactt tgttgaatga taatagaaag caccctaatt gacttggaaa    4534
aaaaaaacag caaaagcaaa gtagcaaca tatgtcaaca tatgtcactg aaataggaaa     4594
cagtcattgg aatgttgcac agaggctaat agctatggac tgttggatac aggatacagt    4654
ggtgagagga gccccatttt aggtctttct tttaggtttt tggttttcat tactccaagt    4714
agcccttgac ccaagaacaa aggcttgttg tatgagttcc actgccagat ttatgggatg    4774
cctggatcat tcagaaggat gcttcaacta ttatttgtca ggtccaaagg tcgtacttga    4834 taacccatt ttctatgtat ggggtagtct aatatattat tttatctact ttatttttcc     4894 ctttttcagaa agtccttagt gcaaaccacc attggaatcc agtcagaaat gtctgtcaga   4954
tagttagaat tgtaacatct aaacctgcca cggatcgaat ggtacttaca ggtacctctc    5014
ttagggactc tgtgatccct aaaatatcag aagaaaatgt ctgtctttct gtccaaatat    5074
ctacttgact tggggta                                                    5092
```

```
<210> SEQ ID NO 2
<211> LENGTH: 1065
<212> TYPE: PRT
<213> ORGANISM: Homo sapiens

<400> SEQUENCE: 2
```

Met Asp Ala Ala Gly Arg Gly Cys His Leu Leu Pro Leu Pro Ala Ala
 1               5                  10                  15

Arg Gly Pro Ala Arg Ala Pro Ala Ala Ala Ala Ala Ala Ala Ala Ser
                20                  25                  30

Pro Pro Gly Pro Cys Ser Gly Ala Ala Cys Ala Pro Ser Ala Ala Ala
            35                  40                  45

Gly Ala Gly Ala Met Asn Pro Ser Ser Ala Gly Glu Glu Lys Gly
        50                  55                  60

Ala Thr Gly Gly Ser Ser Ser Gly Ser Gly Ala Gly Ser Cys Cys
 65                  70                  75                  80

Leu Gly Ala Glu Gly Gly Ala Asp Pro Arg Gly Ala Gly Ser Ala Ala
                85                  90                  95

Ala Ala Gly Ala Ala Ala Leu Asp Glu Pro Ala Ala Gly Gln Lys
            100                 105                 110

Glu Lys Asp Glu Ala Leu Glu Glu Lys Leu Arg Asn Leu Thr Phe Arg
        115                 120                 125

Lys Gln Val Ser Tyr Arg Lys Ala Ile Ser Arg Ala Gly Leu Gln His
    130                 135                 140

Leu Ala Pro Ala His Pro Leu Ser Leu Pro Val Ala Asn Gly Pro Ala
145                 150                 155                 160

```
Lys Glu Pro Arg Ala Thr Leu Asp Trp Ser Glu Asn Ala Val Asn Gly
                165                 170                 175
Glu His Leu Trp Leu Glu Thr Asn Val Ser Gly Asp Leu Cys Tyr Leu
            180                 185                 190
Gly Glu Glu Asn Cys Gln Val Arg Phe Ala Lys Ser Ala Leu Arg Arg
        195                 200                 205
Lys Cys Ala Val Cys Lys Ile Val His Thr Ala Cys Ile Glu Gln
210                 215                 220
Leu Glu Lys Ile Asn Phe Arg Cys Lys Pro Thr Phe Arg Glu Gly Gly
225                 230                 235                 240
Ser Arg Ser Pro Arg Glu Asn Phe Val Arg His His Trp Val His Arg
            245                 250                 255
Arg Arg Gln Glu Gly Lys Cys Lys Gln Cys Gly Lys Gly Phe Gln Gln
        260                 265                 270
Lys Phe Ser Phe His Ser Lys Glu Ile Val Ala Ile Ser Cys Ser Trp
            275                 280                 285
Cys Lys Gln Ala Phe His Asn Lys Val Thr Cys Phe Met Leu His His
        290                 295                 300
Ile Glu Glu Pro Cys Ser Leu Gly Ala His Ala Ala Val Ile Val Pro
305                 310                 315                 320
Pro Thr Trp Ile Ile Lys Val Lys Lys Pro Gln Asn Ser Leu Lys Ala
                325                 330                 335
Ser Asn Arg Lys Lys Lys Arg Thr Ser Phe Lys Arg Lys Ala Ser Lys
            340                 345                 350
Arg Gly Met Glu Gln Glu Asn Lys Gly Arg Pro Phe Val Ile Lys Pro
        355                 360                 365
Ile Ser Ser Pro Leu Met Lys Pro Leu Leu Val Phe Val Asn Pro Lys
370                 375                 380
Ser Gly Gly Asn Gln Gly Thr Lys Val Leu Gln Met Phe Met Trp Tyr
385                 390                 395                 400
Leu Asn Pro Arg Gln Val Phe Asp Leu Ser Gln Glu Gly Pro Lys Asp
                405                 410                 415
Ala Leu Glu Leu Tyr Arg Lys Val Pro Asn Leu Arg Ile Leu Ala Cys
            420                 425                 430
Gly Gly Asp Gly Thr Val Gly Trp Ile Leu Ser Ile Leu Asp Glu Leu
        435                 440                 445
Gln Leu Ser Pro Gln Pro Pro Val Gly Val Leu Pro Leu Gly Thr Gly
    450                 455                 460
Asn Asp Leu Ala Arg Thr Leu Asn Trp Gly Gly Gly Tyr Thr Asp Glu
465                 470                 475                 480
Pro Val Ser Lys Ile Leu Cys Gln Val Glu Asp Gly Thr Val Val Gln
                485                 490                 495
Leu Asp Arg Trp Asn Leu His Val Glu Arg Asn Pro Asp Leu Pro Pro
            500                 505                 510
Glu Glu Leu Glu Asp Gly Val Cys Lys Leu Pro Leu Asn Val Phe Asn
        515                 520                 525
Asn Tyr Phe Ser Leu Gly Phe Asp Ala His Val Thr Leu Glu Phe His
        530                 535                 540
Glu Ser Arg Glu Ala Asn Pro Glu Lys Phe Asn Ser Arg Phe Arg Asn
545                 550                 555                 560
Lys Met Phe Tyr Ala Gly Ala Ala Phe Ser Asp Phe Leu Gln Arg Ser
                565                 570                 575
```

```
Ser Arg Asp Leu Ser Lys His Val Lys Val Cys Asp Gly Thr Asp
            580                 585                 590

Leu Thr Pro Lys Ile Gln Glu Leu Lys Phe Gln Cys Ile Val Phe Leu
            595                 600                 605

Asn Ile Pro Arg Tyr Cys Ala Gly Thr Met Pro Trp Gly Asn Pro Gly
            610                 615                 620

Asp His His Asp Phe Glu Pro Gln Arg His Asp Asp Gly Tyr Ile Glu
625                 630                 635                 640

Val Ile Gly Phe Thr Met Ala Ser Leu Ala Ala Leu Gln Val Gly Gly
                    645                 650                 655

His Gly Glu Arg Leu His Gln Cys Arg Glu Val Met Leu Leu Thr Tyr
            660                 665                 670

Lys Ser Ile Pro Met Gln Val Asp Gly Glu Pro Cys Arg Leu Ala Pro
            675                 680                 685

Ala Met Ile Arg Ile Ser Leu Arg Asn Gln Ala Asn Met Val Gln Lys
            690                 695                 700

Ser Lys Arg Arg Thr Ser Met Pro Leu Leu Asn Asp Pro Gln Ser Val
705                 710                 715                 720

Pro Asp Arg Leu Arg Ile Arg Val Asn Lys Ile Ser Leu Gln Asp Tyr
                    725                 730                 735

Glu Gly Phe His Tyr Asp Lys Glu Lys Leu Arg Glu Ala Ser Ile Ser
            740                 745                 750

Asp Trp Leu Arg Thr Ile Ala Gly Glu Leu Val Gln Ser Phe Gly Ala
            755                 760                 765

Ile Pro Leu Gly Ile Leu Val Val Arg Gly Asp Cys Asp Leu Glu Thr
            770                 775                 780

Cys Arg Met Tyr Ile Asp Arg Leu Gln Glu Asp Leu Gln Ser Val Ser
785                 790                 795                 800

Ser Gly Ser Gln Arg Val His Tyr Gln Asp His Glu Thr Ser Phe Pro
                    805                 810                 815

Arg Ala Leu Ser Ala Gln Arg Leu Ser Pro Arg Trp Cys Phe Leu Asp
            820                 825                 830

Asp Arg Ser Gln Glu His Leu His Phe Val Met Glu Ile Ser Gln Asp
            835                 840                 845

Glu Ile Phe Ile Leu Asp Pro Asp Met Val Val Ser Gln Pro Ala Gly
            850                 855                 860

Thr Pro Pro Gly Met Pro Asp Leu Val Val Glu Gln Ala Ser Gly Ile
865                 870                 875                 880

Ser Asp Trp Trp Asn Pro Ala Leu Arg Lys Arg Met Leu Ser Asp Ser
                    885                 890                 895

Gly Leu Gly Met Ile Ala Pro Tyr Tyr Glu Asp Ser Asp Leu Lys Asp
            900                 905                 910

Leu Ser His Ser Arg Val Leu Gln Ser Pro Val Ser Ser Glu Asp His
            915                 920                 925

Ala Ile Leu Gln Ala Val Ile Ala Gly Asp Leu Met Lys Leu Ile Glu
            930                 935                 940

Ser Tyr Lys Asn Gly Gly Ser Leu Leu Ile Gln Gly Pro Asp His Cys
945                 950                 955                 960

Ser Leu Leu His Tyr Ala Ala Lys Thr Gly Asn Gly Glu Ile Val Lys
                    965                 970                 975

Tyr Ile Leu Asp His Gly Pro Ser Glu Leu Leu Asp Met Ala Asp Ser
            980                 985                 990

Glu Thr Gly Glu Thr Ala Leu His Lys Ala Ala Cys Gln Arg Asn Arg
```

```
                995                1000               1005
Ala Val Cys Gln Leu Leu Val Asp Ala Gly Ala Ser Leu Arg Lys Thr
    1010               1015               1020

Asp Ser Lys Gly Lys Thr Pro Gln Glu Arg Ala Gln Gln Ala Gly Asp
1025               1030               1035               1040

Pro Asp Leu Ala Ala Tyr Leu Glu Ser Arg Gln Asn Tyr Lys Val Ile
            1045               1050               1055

Gly His Glu Asp Leu Glu Thr Ala Val
            1060               1065

<210> SEQ ID NO 3
<211> LENGTH: 55
<212> TYPE: PRT
<213> ORGANISM: Artificial Sequence
<220> FEATURE:
<223> OTHER INFORMATION: Description of Artificial Sequence:Consensus
      sequence (zinc finger)

<400> SEQUENCE: 3

His Xaa Xaa Xaa Xaa Xaa Xaa Xaa Xaa Xaa Xaa Cys Xaa Xaa Xaa
  1               5                  10                 15

Xaa Xaa Xaa Cys Xaa Xaa Xaa Xaa Xaa Xaa Xaa Xaa Xaa Xaa Xaa
            20                 25                 30

Cys Xaa Xaa Cys Xaa Xaa Xaa Xaa Arg Xaa Xaa Cys Xaa Xaa Xaa Xaa
        35                 40                 45

Xaa Xaa Xaa Xaa Xaa Xaa Cys
        50                 55

<210> SEQ ID NO 4
<211> LENGTH: 59
<212> TYPE: PRT
<213> ORGANISM: Artificial Sequence
<220> FEATURE:
<223> OTHER INFORMATION: Description of Artificial Sequence:Consensus
      sequence (zinc finger)

<400> SEQUENCE: 4

His Xaa Xaa Xaa Xaa Xaa Xaa Xaa Xaa Xaa Xaa Xaa Cys Xaa Xaa Cys
  1               5                  10                 15

Xaa Xaa Xaa Xaa Xaa Xaa Xaa Xaa Xaa Xaa Xaa Xaa Xaa Xaa Xaa
            20                 25                 30

Xaa Xaa Xaa Cys Xaa Xaa Cys Xaa Xaa Xaa Xaa His Xaa Xaa Xaa Xaa
        35                 40                 45

Cys Xaa Xaa Xaa Xaa Xaa Xaa Xaa Xaa Xaa Cys
        50                 55

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:Consensus
      sequence (ATP binding site)

<400> SEQUENCE: 5

Gly Xaa Gly Xaa Xaa Gly
  1               5

<210> SEQ ID NO 6
<211> LENGTH: 23
<212> TYPE: DNA
<213> ORGANISM: Artificial Sequence
```

-continued

```
<220> FEATURE:
<223> OTHER INFORMATION: Description of Artificial Sequence:Synthetic
      oligonucleotide

<400> SEQUENCE: 6
tgaatcccaa gagtggaggc aac                                          23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 7
ggaggttcca gcgatctagc tg                                           22

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 8

Cys Ala Gly Gln Lys Glu Lys Asp Glu Ala Leu Glu Glu Lys Leu Arg
 1               5                  10                  15
Asn
```

HUMAN DIACYLGLYCEROL KINASE IOTA

RELATED APPLICATIONS

This application is related to and claims the benefit of United States Provisional Application Ser. No. 60/103,079 of Steven M. Prescott, Li Ding, Elie Traer, Thomas McIntyre, and Guy A. Zimmerman filed Oct. 5, 1998 and entitled "Cloning and Characterization of a Novel Diacylglycerol Kinase, DGKι," which is incorporated herein by this reference.

FIELD OF THE INVENTION

The present invention relates to the isolation and characterization of a novel diacylglycerol kinase (DGK) isoform. More specifically, the invention relates to the isolation of DGKι, which is expressed only in brain and retina.

TECHNICAL BACKGROUND

Lipids are molecules that are fundamental to the existence of all living organisms. Lipids are non-polar molecules that are water-insoluble. As such, the term lipids includes a large number of structurally distinct biomolecules, including phospholipids, glycolipids, and sterols, like cholesterol.

Lipids have a variety of biological roles. First, lipids are the major component of biological membranes. Like exterior walls of houses, biological membranes are structurally organized barriers which define and separate cells from the environment and other cells. Like interior walls of houses, biological membranes are structurally organized barriers that compartmentalize and organize the cell's intracellular components.

Biological membranes, however, are not impervious walls. Instead, they are highly selective permeable barriers which regulate the quality and quantity of molecules which are allowed to pass through the membrane. The cell membrane, for example, tightly regulates the amount of water, ions and sugar which can pass into the cell.

One class of lipids which is abundant in all biological membranes is phosphoglycerides. Phosphoglycerides are comprised of a glycerol (a three-carbon alcohol) backbone, two fatty acid chains (long hydrocarbon molecules), and a phosphate. The simplest phosphoglyceride that can be formed is phosphatidic acid. Phosphatidic acid has two fatty acid chains esterified to the hydroxyl groups at the C-1 and C-2 positions of glycerol, respectively. The C-3 hydroxyl group of glycerol is esterified to phosphoric acid. While phosphatidic acid is not a major component of biological membranes, it is a key intermediate in the formation of structurally related phosphoglycerides such as phosphatidylethanolamine, phosphatidylserine, and phosphatidylinositol, which has a sugar moiety attached to the phosphate.

Second, fatty acid-containing lipids are an energy source for cells and organisms. Fatty acids in a series of biological reactions are oxidized by certain cells to yield large amounts of energy necessary to carry out essential biological functions. Fatty acids used for fuel are stored as triacylglycerols (which are sometimes referred to as "triglycerides"), or neutral fats. Like phosphatidic acids, triglycerides have a glycerol backbone. Rather than having two fatty acid and a phosphate group, however, triglycerides contain three fatty acid chains.

Triglycerides are an efficient way to store large quantities of energy, and thus are the major energy reservoir in humans and other mammals. The complete oxidation of a typical fatty acid yields approximately 9 kcal/g, as compared to about 4 kcal/g for proteins and carbohydrates. Moreover, unlike carbohydrate energy stores, triglycerides are anhydrous (i.e., do not contain water). Consequently, a gram of triglycerides contains more than six times the energy of one gram of carbohydrate. Taken together, triglycerides account for about 80% of all the energy of an average individual.

Finally, lipids participate in cell-cell communication, differentiation and proliferation. Normal development and function in living organisms requires interactions between cells and the molecules in the surrounding environment. One way cells communicate is via molecules, called transmembrane proteins, that span the cell's biological membrane. When the portion of the transmembrane protein which is outside of the cell encounters specific molecules in the surrounding environment, it undergoes conformational changes that trigger a biological cascade inside the cell.

The binding or interaction of a molecule in the environment with a transmembrane protein frequently activates a membrane-bound enzyme called phospholipase C. The activation of phospholipase C is at the center of many major biological events. For example, the activation of phospholipase C is correlated with cell proliferation. Vasopressin, prostaglandin F2, and bombesin, which stimulate cell proliferation, stimulate phospholipase C. In addition, phospholipase C plays a role in activation of T lymphocytes of the immune system and fertilization of eggs.

Phospholipase C exerts its biological effects by catalyzing a reaction which cleaves the sugar moiety of the cell membrane lipid phosphatidylinositol 4,5 bisphosphate. The reaction releases diacylglycerol (DAG) and inositol triphosphate. Diacylglycerol and inositol triphosphate, referred to as second messengers, in turn, activate other molecules within the cell. Diacylglycerol, for example, activates an enzyme called protein kinase C (PKC), which is central to numerous biological processes, including the regulation of cell growth and differentiation.

DAG is at the heart of lipid-mediated biological events. See U.S. Patent application Ser. No. 08/841,483 filed Apr. 22, 1997. Diacylglycerol is a precursor to phosphatidylcholine, phosphatidylethanolamine and phosphatidylinositol, which are indispensable components of biological membranes. In addition, diacylglycerol is a precursor to triglyceride biosynthesis and, therefore, is central to energy stores of organisms. Finally, diacylglycerol is a second messenger which binds and activates protein kinase C, leading to numerous biological events.

The proper regulation of diacylglycerol in cells, therefore, is critical for proper biological function. Abnormally high or low levels of diacylglycerol would be predicted to alter the lipid biosynthesis and the activity of enzymes that depend on diacylglycerol, like PKC.

Diacylglycerol kinase (DGK), which catalyzes phosphorylation of DAG to phosphatidic acid (PA), is thought to be a key enzymes in the regulation of DAG levels and, as a result, to be responsible for attenuating the activation of PKC. For example, a constitutively elevated level of DAG (leading to activated PKC) is common in transformed cells, and experimental overexpression of DGKα decreased the elevated DAG level in ras-transformed fibroblasts. T. Fu et al. (1992), FEBS Lett.307:301–304. This type of experiment suggests that conversion of DAG to PA suppresses a mitogenic signal, but this conclusion is complicated by the fact that PA itself may be mitogenic. W. Moolenaar et al. (1986), *Nature* 323:171–173. PA has been implicated in the regulation of DNA synthesis, in the induction of c-myc, c-fos, and platelet-derived growth factor; in cAMP formation; and in modulating the activity of n-chimaerin and NF1. Thus, since both DAG and PA can act as second messengers, their interconversion is likely to be tightly regulated.

DGK activities have been detected from a variety of tissues and organisms from *Arabidopsis thaliana* and *E. coli* to mammals. Eight mammalian DGKs have been identified and characterized; they differ in their activators, expression patterns, substrate specificity and structural domains. DGKs can be divided into five subfamilies according to distinctive structural motifs. Type I includes DGKα, β, and γ, which have E-F hand motifs at their N-termini and are stimulated by $Ca^{++}$, although the binding affinity for $Ca^+$ differs among these three isoforms. DGKδ and η are type II DGKs; each has a pleckstrin homology domain ("PH domain") at its N-terminus instead of an E-F hand motif. PH domains have been found in a number of proteins involved in signal transduction and serve as sites of protein-protein and protein-phospholipid interactions. The third type of DGK, DGKε, has the simplest structure in the DGK family and shows substrate selectivity for DAG with an arachidonoyl residue at the sn-2 position. Type IV is typified by DGKζ, which has four ankyrin repeats at its C-terminus and a region similar to the MARCKS phosphorylation site domain. The Drosophila DGK2, rdgA gene also belongs to this group, and it is expressed almost exclusively in the retina. I. Masai et al. (1993), *Proc. Natl. Acad. Sci. USA*. 90:11157–11161 ("Masai et al."). A mutation in rdgA causes degeneration of photoreceptor cells and blindness. Id. Interestingly, the photoreceptor cells degenerate regardless of whether the cells are exposed to light or not, implying that Drosophila DGK2, rdgA may be required for more than just a light-signaling cascade, and a recent study showed that the degeneration begins with disruption of organelles responsible for the transportation of phospholipids to the photoreceptor membrane. I. Masai et al. (1997), *J. Neurobiol.* 32:695–706. One of the mutations that results in the retinal degeneration phenotype in Drosophila is a stop codon before the ankyrin repeats, and these motifs are known to mediate protein recognition. V. Bennett (1992), *J. Biol. Chem.* 268:1501–1504. Proteins containing ankyrin repeats are involved in a variety of cellular processes such as gene regulation and cell cycle control. The type V DGK, DGKθ, contains three cysteine-rich repeats instead of the typical two, and a ras-binding domain.

From the foregoing, it will be appreciated that it would be an advancement in the art to identify and characterize nucleic acid sequences that code for enzymes that catalyze the conversion of DAG to PA. It would be a further advancement to identify nucleic acid sequences coding for such enzymes that regulate signal transduction in specific tissues, such as retina and brain. It would be a further advancement in the art to provide methods of detecting DGK mRNA and proteins in a cell. Finally, it would also be an advantage to provide means for regulating cell proliferation by decreasing the pools of diacylglycerol available to activate PKC.

Such nucleic acid sequences and methods are disclosed and claimed herein.

BRIEF SUMMARY OF THE INVENTION

The present invention relates to a novel human DAG kinase (DGK) isoform, DGKι. Provided herein are nucleic acid molecules that encode such DGK molecules. In certain embodiments, the nucleic acid molecules of the present invention comprise the nucleotide sequence for human DGKι (SEQ ID NO: 1). In certain other embodiments, the present invention provides nucleic acid molecules that code for the amino acid sequence of human DGKι (SEQ ID NO: 2). The present invention further provides nucleic acid sequences that code for proteins having diacylglycerol kinase enzymatic activity, wherein the complements of such sequences hybridize to SEQ ID NO: 1.

The present invention also provides recombinant vectors comprising nucleic acid molecules that code for DGKι. In certain embodiments, these recombinant vectors are plasmids. In certain embodiments, these recombinant vectors are prokaryotic or eukaryotic expression vectors. In certain especially preferred embodiments, the nucleic acid coding for DGKι is operably linked to a heterologous promoter.

The present invention further provides host cells comprising a nucleic acid that codes for DGKι.

Further embodiments of the present invention include in vitro methods of using nucleic acids coding for DGKs to decrease intracellular levels of DAG and increase intracellular levels of phosphatidic acid.

These and other advantages of the present invention will become apparent upon reading the following detailed description and appended claims.

SUMMARY OF THE DRAWING

The file of this patent contains at least one drawing executed in color. Copies of this patent with color drawing(s) will be provided by the Patent and Trademark Office upon request and payment of the necessary fee.

A more particular description of the invention briefly described above will be rendered by reference to the appended drawings and graphs. These drawings and graphs only provide information concerning typical embodiments of the invention and are not therefore to be considered limiting of its scope.

FIG. 1C illustrates the alignment of hDGKι C-terminus sequence with the consensus ankyrin repeat sequence. Conservative substitutions are included in the alignment.

FIG. 3A illustrates heterologous expression of DGKι. COS-7 cells were transfected with DGKι cDNA in the pEUK-C1 vector or vector alone. After 48 h, the cells were harvested and examined by western blot analysis for the expression of DGKι with polyclonal rabbit antibody against DGKι. 20 μg of protein of the COS-7 cell homogenate were loaded in each lane. In the control experiment, pre-incubation with the immunogen-peptide significantly blocked the recognition of the DGKι protein. COS-7 cells transfected with hDGKι in an expression vector express a 130 kDa protein.

FIG. 3B illustrates the subcellular localization of DGKι. COS-7 cells were transfected with DGKι cDNA in the pELUK-C1 vector. After 48 h, the cells were harvested and separated into cytoplasmic and nuclear fractions. 10 μg of protein from each fraction was loaded in each lane. Human Acyl-CoA synthetase 4 antibody was used as a control to ensure the purity of each fraction. Y. Cao et al. (1998), *Genomics* 49:327–330. Human Acyl-CoA synthetase 4 has been demonstrated to be a cytoplasmic protein (personal communication). DGKι localizes in both cytoplasm and nucleus.

FIG. 3C illustrates the effect of various PKCs on the nuclear localization of DGKι. COS-7 cells were transfected with DGKι in combination with PKCα, PKCβ, or PKCγ. After 48 h, the cells were harvested and separated into cytoplasmic and nuclear fractions. 10 μg of protein from each fraction was loaded in each lane. An antibody to Acyl-CoA synthetase 4, which was previously showed to be cytoplasmic was used as a control to ensure the purity of each fraction. The nuclear localization of DGKι is attenuated by PKCα and PKCγ, but not PKCβ.

DETAILED DESCRIPTION OF THE INVENTION

Figure 1A:
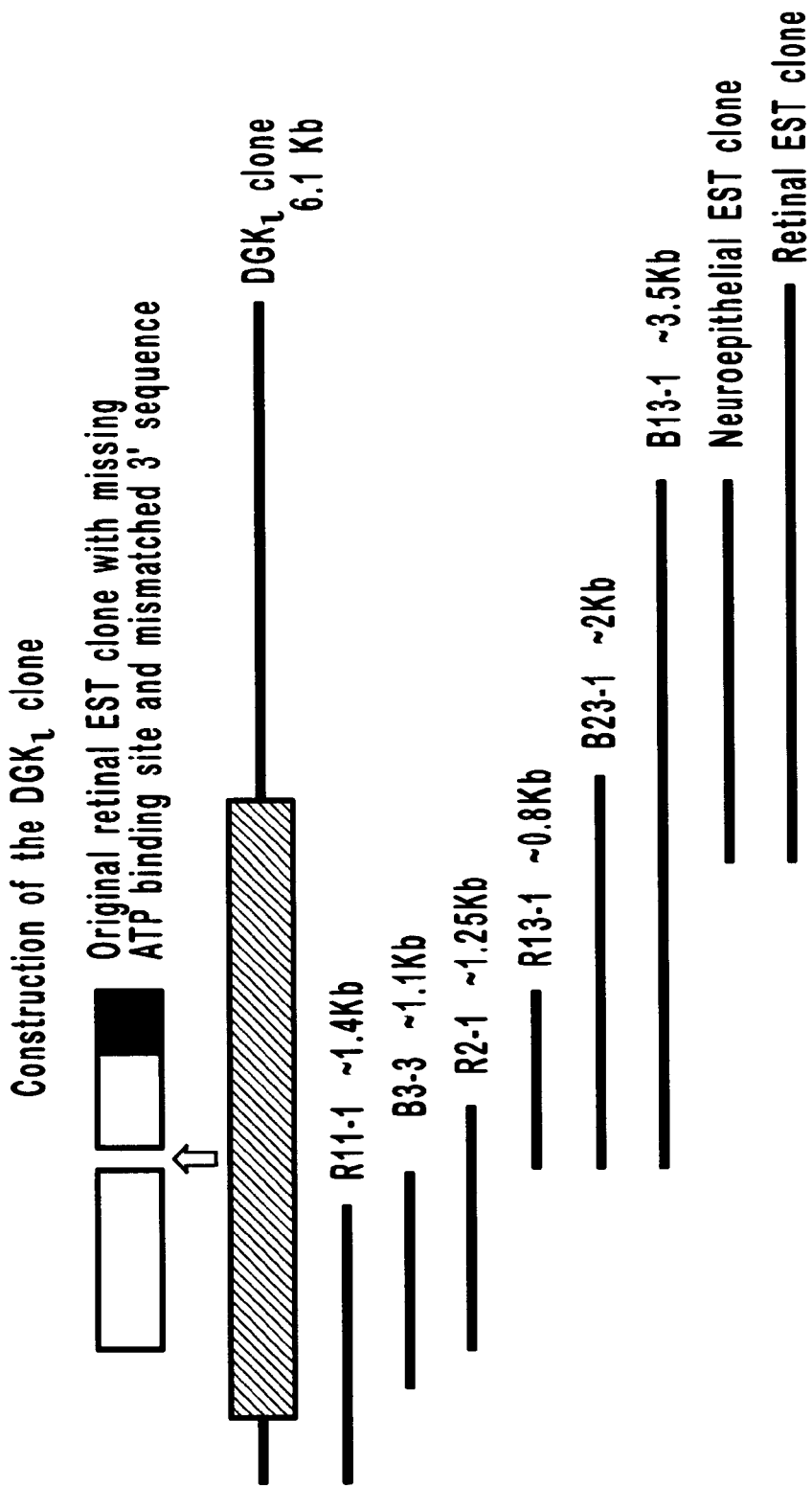
FIG. 1A schematically illustrates the overlapping map of representative cDNA clones obtained by screening retina and brain libraries with a variety of probes.

The present invention relates to cDNA and genomic clones for a novel DGK. More particularly, the present inventions relates to the isolation and characterization of DGKι (SEQ ID NO: 1). DGKι expression in retina and brain suggests that this enzyme may have an important function in vision.

DGKs catalyze the conversion of DAG to phosphatidic acid, which likely is relevant to two important cellular functions: it is a crucial step in the synthesis of phospholipids and also serves to turn off signals transduced through DAG. The latter is likely to be the explanation for the presence of multiple isoforms, since compartmentalization of signals and the relevant enzymes has been shown in many systems. Both DAG and phosphatidic acid can have signaling functions and, since DGK catalyzes this reaction, it may play a pivotal role in regulation of signaling through the PI pathway. In support of this, the Drosophila mutation rdgA causes retinal degeneration within a week of eclosion. The lack of catalytic function was confirmed by measuring the levels of DAG, which were found to be near normal, and PA, which were markedly reduced. H. Inoue et al. (1989), *J. Biol. Chem.* 264:5996–6000. This result from Drosophila suggests that human DGKι may be important for the production of PA in retina, which has a relatively high amount of PA compared to other tissues. Mutations in PI-specific phospholipase C (PLC), DGK2, and PKC all have been found to cause retinal degeneration in Drosophila, so other members of this signaling pathway have similar phenotypes. A corresponding mutation has not yet been found in humans, but the PI cycle and the PKC signaling pathway are well-conserved between insects and mammals, and our identification of DGKι may help to elucidate retinal signaling pathways.

The present invention also provides nucleic acid molecules that code for the amino acid sequence of the human DGKι enzyme (SEQ ID NO: 2). The present invention further provides nucleic acid sequences that code for proteins having diacylglycerol kinase enzymatic activity, wherein the complement of such sequences hybridize to SEQ ID NO: 1 under the conditions of 65° C. overnight in a solution comprising 5×SSPE, 5×Denhardt's, 0.2% SDS, and 0.1% $Na_2P_4O_7$, followed by washing twice in 0.6× SSPE, 0. 1% SDS, and 0. 1% $Na_2P_4O_7$ at 65° C. for 30 minutes.

The present invention also provides recombinant vectors comprising nucleic acid molecules that code for DGKι. Recombinant vectors may be, e.g., plasmids, recombinant phages or viruses, transposons, cosmids, or artificial chromosomes. Such vectors may further include elements that control the replication and expression of the DGKι nucleic acid sequences. Such vectors may also include sequences (such as antibiotic resistance genes) that allow for the screening or selection of cells containing the vector. In certain preferred embodiments, recombinant vectors of the present invention are plasmids. In certain embodiments, these recombinant vectors are prokaryotic expression vectors. In certain other embodiments, these recombinant vectors are eukaryotic expression vectors. In certain especially preferred embodiments, the nucleic acid coding for DGKι is operably linked to a heterologous promoter.

The present invention further provides host cells comprising a nucleic acid that codes for DGKι. Such host cells may be prepared by transfecting an appropriate nucleic acid into a cell using transfection techniques that are known in the art. These techniques include, e.g., calcium phosphate co-precipitation, microinjection, electroporation, liposome-mediated gene transfer, and high velocity microprojectiles.

Further embodiments of the present invention include in vitro methods of using nucleic acids coding for DGKs to decrease intracellular levels of DAG and increase intracellular levels of phosphatidic acid.

In order to better describe the details of the present invention, the following discussion is divided into four sections: (1) isolation of a cDNA encoding DGKι; (2) tissue distribution of DGKι; (3) heterologous expression and subcellular localization of DGKι; (4) isolation of a genomic clone and chromosomal localization of human DGKι; and (5) sequence modifications.

Isolation of a cDNA Encoding DGKι

The cDNA sequence from DGKζ was used to perform a BLAST search against the EST database. A sequence from a retina library was found that was similar to the cysteine-rich repeats region of DGKζ, but the sequence appeared to be a novel DGK. To further analyze this EST (I.M.A.G.E. Consortium Clone ID 437714), we sequenced it completely; it was 1.9 kb in length and contained two cysteine-rich repeats and part of the conserved DGK catalytic domain, and was similar to DGKζ. However, there was a deletion in the catalytic domain that included a portion of the ATP binding site (FIG. 1A), which would have rendered it inactive. Additionally, the 3' sequence of this clone was not homologous to DGKζ, M. Bunting et al. (1996), *J. Biol. Chem.* 271:10230–10236 ("Bunting"), and an unexpected early stop codon was found. Thus, although this clone appeared to be a novel DGK, it was not clear that it encoded a functional enzyme; however, we hypothesized that the partial deletion of the catalytic domain and other uncommon features might have resulted from aberrant splicing. To test this, we used the EST clone as a probe to search for the putative novel DGK in a retina library. Our first retina library screening yielded two clones, R11-1 and R13-1 (FIG. 1A). Clone R11-1, which was approximately 1.4 kb, overlapped the EST clone and continued about 700 bp upstream. It contained a putative translation start site and an in-frame stop codon 30 bp upstream from the ATG site. The second clone, R13-1 (approximately 0.8 kb) contained the full catalytic domain, including the missing ATP binding site. The sequence of this clone that was 3' to the catalytic domain shared regions of identity with DGKζ and lacked the early stop codon of the EST clone, but was incomplete. To find the full open reading frame, millions of recombinant phages from several retina libraries were screened and several more clones were isolated (e.g. clone R2-1; FIG. 1A) but none of them contained a substantial 3' extension.

At this point, we performed a Northern blot to define other potential sources from which to clone DGKι (see below) and, based on this result, we subsequently screened a human brain cDNA library to obtain the full sequence. Using clones R11-1 and R13-1 as probes, 14 positives were found from two separate screenings. Clone B23-1 (approximately 2 kb) overlapped with clone R13-1 and contained the missing coding sequence at the 3' end. Four ankyrin repeats and a stop codon were found in this clone. Another clone, B13-1, (approximately 3.6 kb), had about 1.6 kb of 3' untranslated sequence but did not contain a poly(A) tail. Clones B23-1 and B13-1 were used to do further searches against the EST database, which revealed additional clones that contained more 3' untranslated region (UTR) sequence. These were obtained and sequenced; the overlapping map of all the cDNAs is shown in FIG. 1A.

Figures 1, 1B, 2:
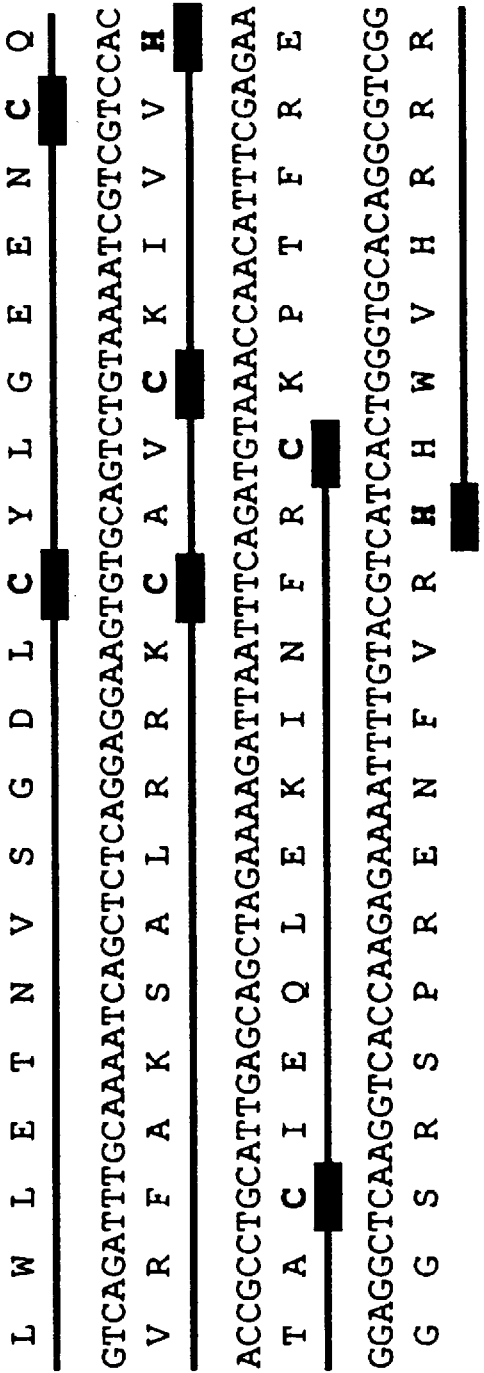
FIG. 1B illustrates the nucleic acid sequence and deduced amino acid sequence of hDGKι. The zinc fingers are underlined, and conserved cysteine and histidine residues are marked with solid boxes. Serine residues with the MARCKS homology region are marked by open circles. The residues within the ATP-binding motif are double underlined.

The combined sequence revealed a DGK with an open reading frame of 3198 nucleotides, and a predicted protein that would contain 1065 amino acids. We designated this isoform iota (ι). Like other DGKs, it contained the conserved cysteine-rich repeats near the N-terminus and the typical DGK catalytic domain. The first and second cysteine-rich repeats included the motifs $HX_{11}CX_6CX_{12}CX_2CX_4RX_2CX_{10}C$ (SEQ ID NO: 3) and $HX_{11}CX_2CX_{19}CX_2CX_4HX_4CX_9C$ (SEQ ID NO: 4), respectively (FIG. 1B). DGKι has a conserved putative ATP binding site, GXGXXG (SEQ ID NO: 5) (FIG. 1B). Mutation of the second glycine in Drosophila DGK2 causes the rdgA phenotype. DGKι did not contain the E-F hand motifs present in the type I DGKs, so presumably would not be stimulated by $Ca^{++}$.

The proteins that are most closely related to hDGKι are hDGKζ (72% similarity, 63% identity) and the Drosophila DGK2, rdgA, (49% similarity, 40% identity). Like DGKζ, DGKι contains a region that is similar to the phosphorylation site domain from MARCKS (RKKKRTSFKRKASKR; amino acids 339 to 353 of SEQ ID NO: 2), which has been shown to serve as a nuclear localization signal and PKC phosphorylation site in DGKζ. M. K. Topham et al. (1998), *Nature* 394:697–700 ("Topham et al.") Like both DGKζ and Drosophila rdgA, DGKι contains four ankyrin repeats near the C-terminus. A comparison of the ankyrin repeats among DGKι, DGKζ and rdgA is shown in FIG. 1C. The domain with multiple ankyrin repeats, which has been shown to be crucial for the function of Drosophila DGK2 rdgA, is the dominant structural feature that defines DGKι, DGKζ, and dDGK2 rdgA as members of a subfamily. A Drosophila DGK2 nonsense mutation in the linker region between the catalytic domain and the ankyrin repeats leads to a truncated protein and causes the mutant phenotype. Although the exact function of the ankyrin repeats in mammalian type IV DGKs is not known, these sequences in other proteins have been implicated in a variety of cellular regulatory processes including protein-protein interaction, gene regulation, and cell cycle control. The similar pattern of tissue expression between DGKι and Drosophila DGK2 suggests that the ankyrin repeats may play an important role in the function of DGKι as they do in Drosophila DGK2.

A potential explanation for the high similarity between DGKι and DGKζ is that they may have resulted from gene duplication during evolution. In *C. elegans* and Drosophila, there appears to be only a single isoform of the type IV DGKs based upon homology searches (not shown). The product of such a duplication could lead to the two genes, DGKι and DGKζ, which share great similarity between their sequences and motifs, yet have distinct expression patterns and markedly different sizes of their messenger RNA. DGKι was shown to be expressed exclusively in brain and retina by Northern blot and RT-PCR, whereas DGKζ is produced abundantly in many tissues. The mRNAs of DGKζ are about 3.7 kb and 4.2 kb in length, while the message of DGKι is >12 kb and includes a very long 3' UTR. Worthy of note is that Drosophila DGK2 also has a long message length of 9 kb, and 3' UTR sequences have been found to be involved in both transcriptional and post-transcriptional regulation. It is possible that DGKι and Drosophila DGK2, rdgA UTR sequences are involved in the regulation of their tissue-specific expression and the stability of their messages. Despite the similarity in the coding sequence of DGKι and DGKζ, the size of DGKι message is much larger than DGKζ as a result of the long 3' UTR sequence. Interestingly, this portion of the DGKι sequence is more similar to the rdgA gene, for which the mRNA is approximately 9 kb, than to human DGKζ.

Tissue Distribution of DGKι

Figure 2A:
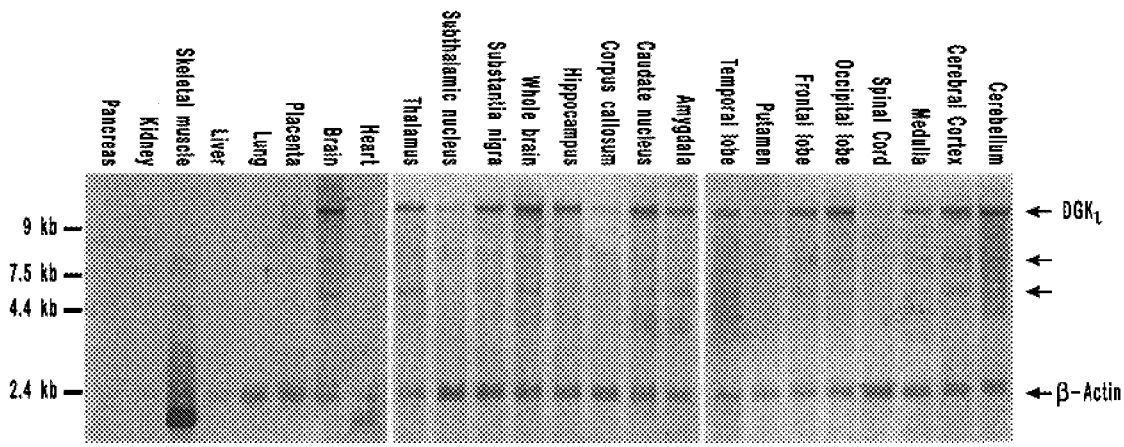
FIG. 2A is a photograph of Northern blots demonstrating that DGKι is expressed in the brain. A filter with mRNA from eight different human tissues and two filters with mRNA from different regions of human brain were probed with a fragment of hDGKι, clone R13-1. Under stringent hybridization and washing conditions, one major band at >12 kb was detected in the sample from total brain and different regions of brain. No signals were detected in other tissues. A β-actin probe was used as a positive control for the amount of the mRNA loaded and the integrity of the mRNA in each lane.

We analyzed a variety of human tissues by Northern blot to determine the size and expression pattern of hDGKι. We found that DGKι was expressed only in brain among the eight tissues examined and the size of the mRNA was ≧12 kb. Weak signals at about 9.5 kb and 7.5 kb also were detected. (FIG. 2A).

Figure 2B:
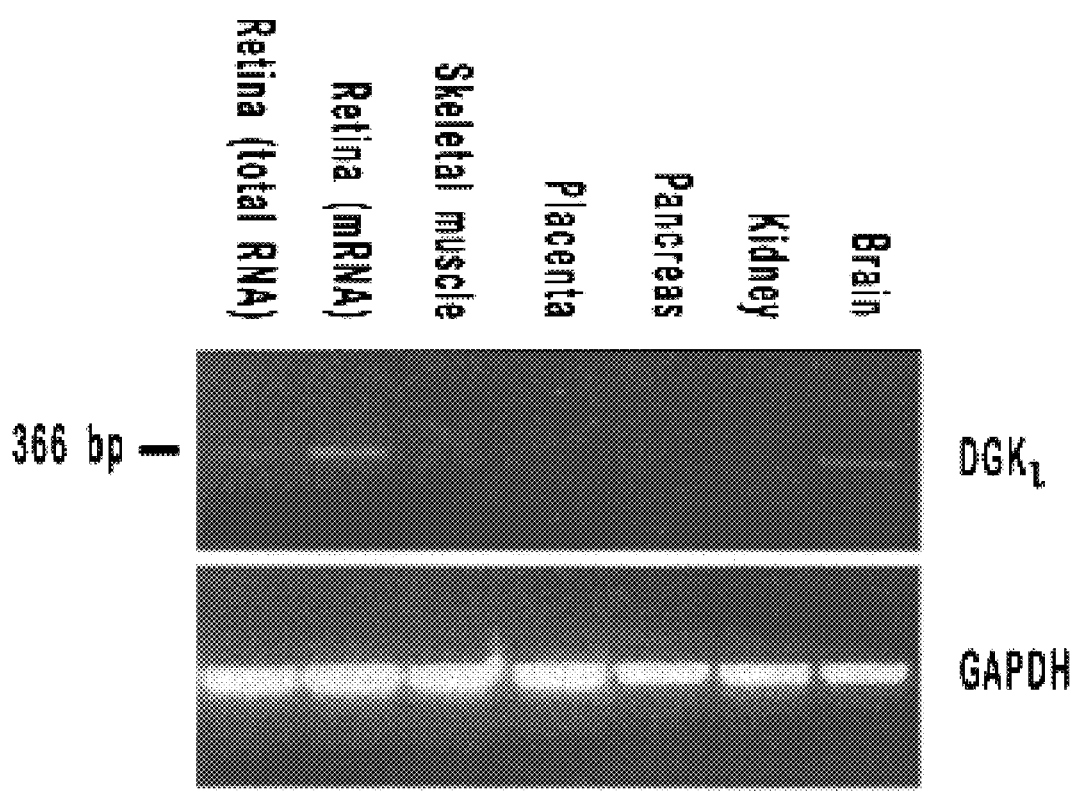
FIG. 2B is a photograph of reverse-transcribed PCR products separated by gel electrophoresis. RNAs from different tissues were reverse-transcribed to produce single-strand cDNA. The cDNA was used for PCR amplification with primers specific for DGKι, which should give a specific product of 366 bp. GAPDH primers were used as positive controls for the PCR reaction. Parallel reactions without template gave no product (not shown).

In contrast, hDGKζ mRNA was present in all eight tissues at sizes of 3.7 kb and 4.2 kb. See Bunting et al. We next examined samples from specific regions of human brain and found DGKι mRNA in almost every region, but in different amounts. It was highly expressed in hippocampus, caudate nucleus, occipital pole, cereberal cortex and cerebellum. Therefore, DGKι has a more restricted expression pattern than DGKζ, despite the similarity of their domain motifs. Since our original clone was described in a retina library, and because rdgA is highly expressed in Drosophila retina, we suspected that DGKι is expressed in human retina. To assess this, we used RT-PCR to amplify a 366 bp fragment from the catalytic domain region of the DGKι and found expression exclusively in human retina and brain. No signals were detected even after 35 cycles of the PCR reaction in samples from pancreas, placenta, kidney and skeletal muscle. The GAPDH control primers amplified relatively equally from all samples (FIG. 2B). This result confirmed the results from our Northern blots and added additional evidence that rdgA and human DGKι are orthologs since their tissue distribution, like their primary structure, is conserved.

Heterologous Expression and Subcellular Localization of DGKι

To test whether the cloned DGKι encodes a functional DGK, we subcloned two EcoRI fragments containing the entire coding sequence of DGKι into a mammalian expression vector. We also developed an antibody to a unique peptide from the predicted amino acid sequence. The cDNA expression construct was transfected into COS-7 cells and homogenates were prepared for both enzymatic assay and immunoassay. A protein with an apparent molecular weight of about 130 kDa was recognized by the peptide antibody in extracts of the transfected cells. The molecular weight of the protein expressed from the DGKι cDNA compares favorably with the predicted size of 117 kDa. Extracts from cells transfected with the vector alone or with no DNA did not react with the antibody. Furthermore, pre-incubation of the peptide antigen with the antibody blocked the recognition of the 130 kDa protein, confirming that the interaction was specific (FIG. 3A). Thus, the predicted translation start site can be used effectively to make a 130 kDa protein.

In other work, Topham et al. found that the region in DGKζ that is homologous to the MARCKS phosphorylation site domain can function as a nuclear localization sequence. Since DGKι has this same sequence (FIG. 1B), we predicted that a portion of the enzyme would be found in the nucleus. To test this prediction, homogenates from transfected COS-7 cells were separated into cytoplasmic and nuclear fractions that were analyzed by immunoblotting. An antibody against a cytoplasmic protein was used as a control to ensure the purity of each fraction. About one-quarter to one-third of the DGKι was found in the nuclear fraction, with the majority in the cytoplasm (FIG. 3B). This result demonstrated that DGKι is distributed between the cytoplasm and nucleus. The MARCKS protein is a major substrate for protein kinase C in all cells. Our research group recently showed that residues in the MARCKS phosphorylation site domain in DGKζ are targets for PKCα and γ, but not other isoforms, and that this phosphorylation results in exclusion of the DGK from the nucleus. See Topham et al. We questioned whether the nuclear localization of DGKι also is regulated by PKC. We cotransfected DGKι with one of the three PKC isoforms (PKCα, β, or γ) into COS-7 cells, respectively. Homogenates from transfected COS-7 cells were separated into cytoplasmic and nuclear fractions, which were analyzed by immunoblotting. We found that the nuclear localization of DGKι was lost when PKCα or PKCγ were co-expressed, but not with PKCβ expression (FIG. 3C). Thus, as with the related isoenzyme, DGKζ, the subcellular localization of DGKι is regulated by specific isoforms of PKC.

Our data show that a majority of DGKι protein is located in the cytoplasm, with a smaller fraction in the nucleus. The existence of a potential nuclear export signal at $L^{442}$–$L^{450}$ may explain this bimodal distribution. Alternatively, the nuclear localization of DGKι may be regulated by phosphorylation in much the same manner as DGKζ, in which phosphorylation by PKC attenuates the nuclear localization. With DGKζ, the nuclear localization attenuates the accumulation of DAG in response to a mitogenic stimulus. DGKι may have a similar effect, which could affect growth and differentiation.

Figure 4:
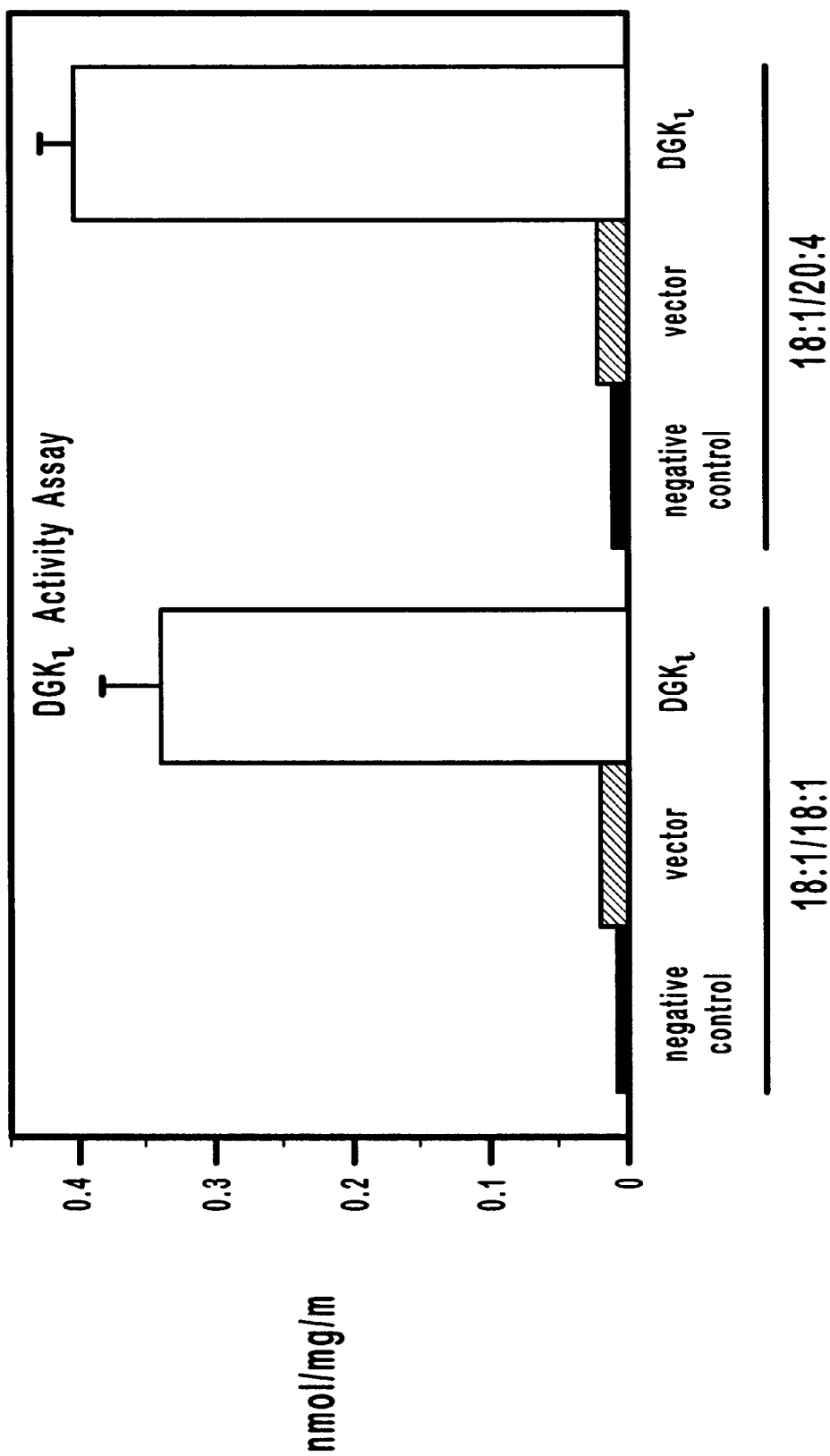
FIG. 4 is a bar graph illustrating the substrate utilization of DGKι. COS-7 cells were transfected with a hDGKι expression construct or vector alone. The homogenates were assayed for DGK activity as described below in Example 5. The DGK activity in cells transfected with DGKι was 18-fold higher than those with vector alone and 36-fold higher than background. DGKι did not display preference in utilizing arachidonoyl-containing DAG. The result represents the mean of the values obtained in duplicate experiments. The error bars indicate the standard deviation.

Homogenates from cells transfected with the DGKι cDNA or vector alone were assayed for DGK enzymatic activity. The cells transfected with DGKι showed much greater activity than those transfected with vector alone or nontransfected cells, which demonstrated that hDGKι encodes a functional enzyme. We tested two different substrates and found that DGKι displayed an enzymatic activity pattern similar to DGKζ in that DGKι utilized 1,2 dioleoyl-sn-glycerol and 1-stearoyl-2-arachidonoyl-sn-glycerol equally well (FIG. 4). That is, DGKι (unlike DGKε) has no preference for DAG with an arachidonoyl residue at sn-2 position.

Isolation of a Genomic Clone and Chromosomal Localization of Human DGKι

The DGKι cDNA was used to isolate a genomic clone from a human Bac library. The human DGKι gene is divided into 35 exons, with the initiation codon being present in exon 2.

Figure 5A:
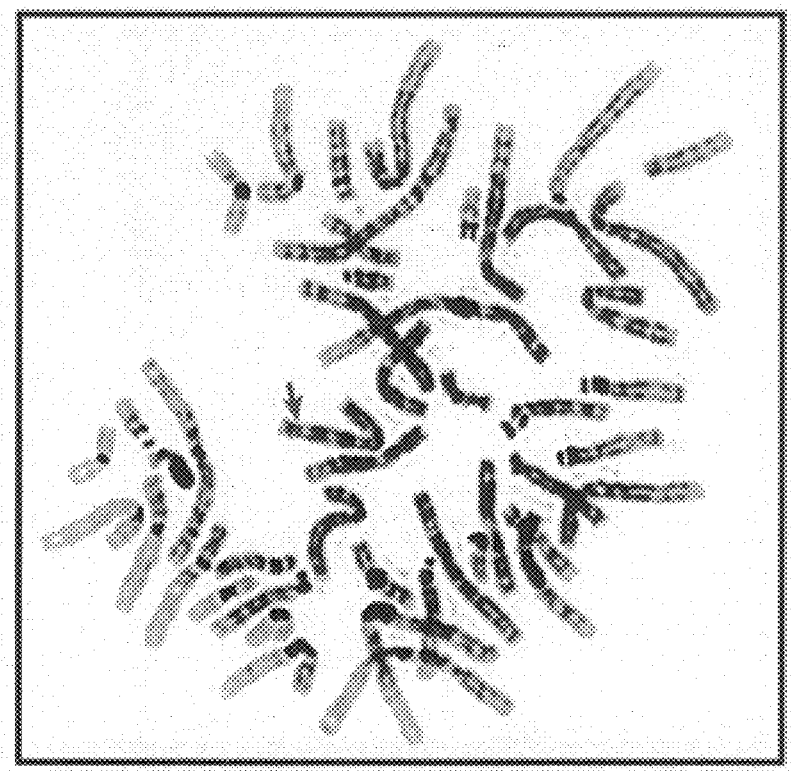
FIG. 5 illustrates the chromosomal localization of DGKι. A Bac genomic clone of DGKι was used as a probe to perform fluorescence in situ hybridization. The arrows indicate the physical location of DGKι. It was mapped to chromosome 7q32.3-33.
Figure 5B:
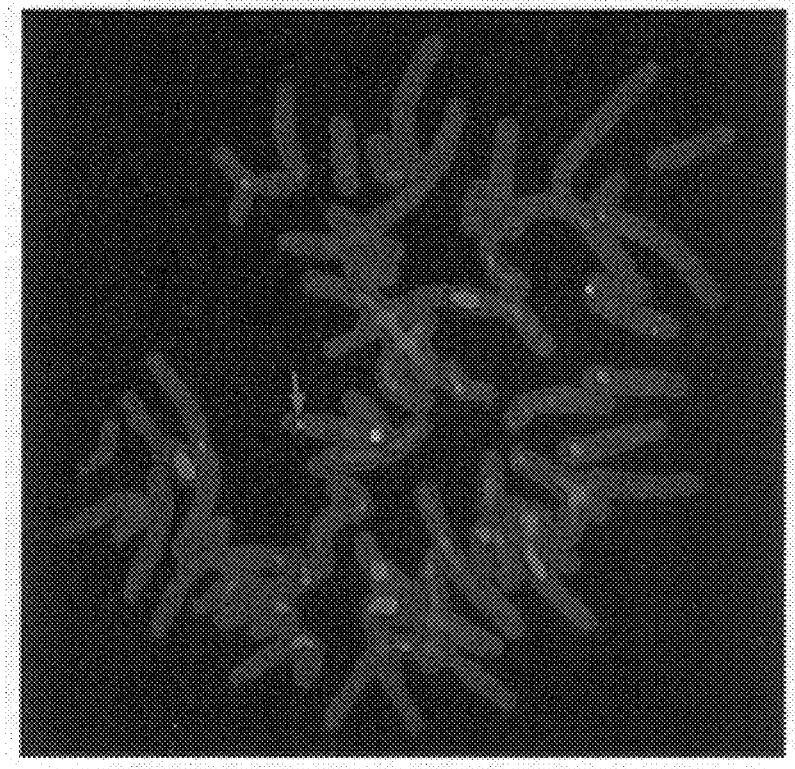

To determine the physical location of the DGKι gene, we performed fluorescence in situ hybridization using the Bac clone as a probe and found that it localized to chromosome 7q32.3-33 (FIG. 5). Interestingly, a dominant form of retinitis pigmentosa 10 has been genetically mapped to a locus in the same chromosomal region, 7q32.3-33, as we found for DGKι, which suggests it as a candidate gene for this disorder.

Sequence Modifications

Included within the scope of the present invention are modifications of the nucleic acid sequences described herein. Such modifications include those that do not affect the corresponding protein sequence, e.g., mutations in a non-coding region. Modifications of the coding region may also be made without affecting the corresponding protein sequence. It is well known to those of skill in the art that the genetic code is redundant; that is, many nucleic acid triplets (called "codons") code for the same amino acid. For example, the codons CUU, CUC, CUA, CUG, UUA, and UUG all specify the amino acid leucine. Likewise, GAA and GAG specify glutamic acid. Thus, by changing a GAA codon to GAG, the corresponding protein sequence is unaffected.

Modifications of a nucleic acid sequence also include those that affect the coding sequence for the corresponding protein. Modifications of a protein sequence can be subdivided into three general classes: substitutions, additions, and deletions. These general groups apply to both the nucleic acid and amino acid sequences of the DGK isoforms. While protein modifications may occur naturally, most often protein modifications are deliberately engineered into the nucleic acid sequence that codes for the protein. Protein modification techniques such as site-directed mutagenesis are well known in the art and in many cases are commercially available as kits complete with instructions from, for example, Amersham and Bethesda Research Laboratories.

It is well known in the art that amino acid substitutions may be made without significantly altering the protein's function. Substitutions as defined herein are modifications made to the native nucleic acid or amino acid sequence of a protein or domain which yield a recombinant protein or domain which contains a different amino acid sequence than the native protein or domain without significantly altering its biological function. The most favorable substitutions occur when an amino acid is substituted with a similar or "conserved" amino acid. Conserved amino acids are defined as natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; and the negatively charged amino acids Asp and Glu represent groups of conservative amino acids. This list is not exhaustive. For example, it is well known that Ala, Gly, Ser and sometimes Cys can substitute for each other even though they belong to different groups.

Conservative amino acid substitutions are not limited to naturally occurring amino acids, but also include synthetic amino acids. Commonly used synthetic amino acids are ω amino acids of various chain lengths and cyclohexyl alanine, which are neutral non-polar analogs; citulline and methionine sulfoxide, which are neutral non-polar analogs; phenylglycine, which is an aromatic neutral analog; cysteic acid, which is a positively charged analog; and ornithine, which is a positively charged amino acid analog. Like the naturally occurring amino acids, this list is not exhaustive, but merely exemplary of the substitutions that are well known in the art.

Whether an amino acid can be substituted at all, or whether it can only be substituted by a conserved amino acid is best determined by comparing the amino acid sequence of one or more members of the protein family. Amino acids that are identical in all the members of a protein family usually cannot be substituted. Amino acids which are conserved can usually be substituted by other conserved amino acids without significantly affecting the protein's function. Finally, amino acids which are not conserved within a family can usually be freely substituted.

It will be appreciated by one skilled in the art, that a comparison of the amino acid sequences of the DGK isoforms of the present invention with other DGK proteins indicates that many amino acid substitutions can be made without destroying these kinases' catalytic activity. The human DGKι protein, for example, is 63% and 40% identical to human DGKζ and Drosophila rdgA, respectively.

It will also be appreciated by one skilled in the art that proteins may be comprised of distinct domains. For example, as discussed above, the DGKι protein comprises two cysteine-rich repeats, a conserved catalytic domain, and four ankyrin repeats. A comparison of the amino acids in these domains reveals an even greater degree of conservation than do the sequences for the entire proteins. For example, DGKι shares the greatest amount of homology with other DGKs in the catalytic domain.

Even within domains, subdomains, motifs, however, there are amino acids that are highly conserved and others that are poorly conserved. It will be appreciated that using an amino acid sequence alignment like the one shown in FIG. 1C, one skilled in the art can predict, with a high degree of certainty, which amino acids can be substituted without destroying the protein or domain's biological activity. Similar alignments for various domains can be easily generated using computer programs well known in the art, such as GenBank™/EMBL Databank comparison and alignment programs.

Protein modifications may also occur through deletions. Deletions as defined herein are modifications made to the native nucleic acid or amino acid sequence of a protein or domain which produce a recombinant protein or domain containing at least one amino acid less than the native amino acid sequence of the protein or domain without significantly altering its biological function.

Also included within the scope of the present invention are additions. Additions as defined herein are modifications made to the native nucleic acid or amino acid sequence of a protein or domain which yield a recombinant protein or domain containing at least one amino acid more than the native amino acid sequence of the protein or domain without significantly altering its biological function. For example, a nucleic acid coding for a FLAG epitope may be added to cDNA molecules to facilitate identification or isolation of the corresponding protein. Such epitopes do not substantially alter the corresponding protein's biological function. Similar additions are routinely employed in the art and are not expected to alter the biological function of the protein.

All publications, patents, and patent applications cited in this application are hereby incorporated by reference.

Materials and Methods

[γ-$^{32}$P)ATP (6000 Ci/mmol), [α-$^{32}$P]dCTP (6000 Ci/mmol), ECL detection reagents and Hybond-N nylon membrane were purchased from Amersham. A human retina 5'-STRETCH cDNA library (λgt11, oligo(dT)+random primed), human brain 5'-STRETCH plus cDNA library (λgt11, oligo(dT)+random primed), pEUK-C1 expression vector and human multiple tissue Northern blot were purchased from Clontech. DMEM, penicillin, streptomycin, lipofectAMINE and BenchMark™ prestained protein ladder were from GibcoBRL, and fetal bovine serum (FBS) was from Hyclone Laboratories (Logan, Utah). Leupeptin, pepstatin, aprotinin, soybean trypsin inhibitor and RNase inhibitor were purchased from Boehringer Mannheim. Avanti Polar Lipids provided phosphatidylserine and phosphatidic acid; all other lipids were from Serdary. Octyl-β-glucopyranoside (ULTROL Grade) was purchased from Calbiochem. ATP and phenylmethylsulfonyl floride (PMSF) were purchased from Sigma. Horseradish peroxidase-conjugated goat F(ab')$_2$ anti-rabbit immunoglobulin antibody were from Biosource International.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1

EST (Expressed Sequence Tag) Search

A DGKζ cDNA sequence was used to perform a BLAST search against the EST database. An EST clone (Genbank accession H37913) was found which was similar to the cysteine-rich region of the DGK family, but its nucleotide sequence was distinct. The EST purchased from ATCC was I.M.A.G.E. Consortium CloneID 437714 and was obtained from the I.M.A.G.E. Consortium (LLNL) cDNA. This cDNA clone was sequenced and used to probe other libraries.

Example 2

Isolation and Characterization of cDNAs

One million phage recombinants were plated from a human retina cDNA library (Clontech). All plaques were transferred to hybond-N nylon membranes (Amersham), which were screened with two HindIII and XhoI digested EST fragments. Membranes were prehybridized (4 h; 65° C.) in 5×SSPE, 5×Denhardt's, 0.2% SDS, and 0.1% $Na_2P_4O_7$. Hybridization was performed (overnight; 65° C.) in the same solution. The membranes were washed twice in 0.6×SSPE, 0.1% SDS, and 0.1% $Na_2P_4O_7$ (30 min; 65° C.). Two positives were isolated from the screening. These two positives were released from λgt11 vector by EcoRI, subcloned into pBluescriptII and sequenced. This library was screened once more by using these two clones as probes. Since the 3' coding sequence is missing in these clones, the first two isolated clones were further used as probes to screen a human brain λgt11 cDNA library (Clontech) to obtain the full-length sequence. Over 2 million clones were plated and screened as described previously. Positives were isolated and subcloned into pBluescriptII. The 3' coding sequence was found from this screening. More clones containing longer 3' UTR sequence were found by brain library screening and EST searches using sequences obtained from isolated clones.

Example 3

Northern Blotting

Clone R13-1, containing the sequence around the catalytic domain region of DGKι in a pBluescriptII vector, was linearized by HindIII and used as a template for digoxigenin-labeled riboprobe synthesis. The human multiple tissue Northern blot and human multiple brain Northern blots were performed by using this probe following the procedure described in M. Bunting et al. (1996), *J. Biol. Chem.* 271:10230–10236 ("Bunting et al.").

Example 4

Reverse Transcription-Polymerase Chain Reaction (RT-PCR)

Two μg total RNA from human brain, kidney, pancreas, placenta and skeletal muscle (Clontech) and about 0.5 μg mRNA (Clontech) and total RNA from retina were used for cDNA synthesis. Total RNA from human retinal sample was extracted by using the guanidinium thiocyanate extraction method. RNA samples were heated for 5 min at 90° C. before cDNA synthesis reactions, which were performed in 20 μl reaction with 50 mM Tris-HCl, pH 8.3, 3 mM $MgCl_2$, 75 mM KCl, 10 mM DTT, 0.5 mM dNTPs, 2.5 mM oligo(dT), 40 U RNase inhibitor and 200 U M-MLV reverse transcriptase for 1 hour at 37° C. The reactions were diluted into 130 μl DEPC-treated $H_2O$, and 10 μl of the dilution was used for each PCR amplification. The primers used for amplifying DGKι are: LD 23-1, 5'-TGAATCCCAAGAGTGGAGGCAAC-3' (SEQ ID NO: 6); and LD 23-2, 5'-GGAGGTTCCAGCGATCTAGCTG-3' (SEQ ID NO: 7).

The primers were chosen from different exons to avoid amplifications from potential contamination of genomic DNA in the RNA samples. Glyceraldehyde-phosphate dehydrogenase (GAPDH)-specific primers were used as control primers. The PCR reactions were carried out for 35 cycles as following: 94° C., 30 s; 65° C., 30 s; 72° C., 30 s.

Example 5

COS-7 Transfection and DGK Assay

Human DGKι cDNA clones were subcloned into pEUKC-Cl (Clontech) in the forward orientation. Some of the UTR sequence was not included- COS-7 cells in P35 dishes were transfected with 1 μg of DGKι-containing pEUK-Cl plasmid DNA and 5 ml lipofectamine according to the manufacturer's instructions (Life Technology Inc.). The cells were harvested after 48 h of incubation and scraped into lysis buffer (20 mM Tris-HCl, pH 7.5, 0.25 M sucrose, 1 mM EDTA, 4 mM EGTA, 1 mM DTT, 1 mM PMSF, 20 μg/ml of leupeptin, pepstatin, aprotinin and soybean trypsin inhibitor). All homogenates were frozen and stored at −70° C. until assayed. The DGK assay was performed as previously described in Bunting et al. In the PKC cotransfection experiment, 500 ng of DNA encoding PKCα, β, or γ (in PCDNA3/Amp; a gift from J. Metherall, University of Utah) were combined with 500 ng of full-length DGKι. Cells were transfected as described in Bunting et al.

Example 6

Antibody Production, Cell Fraction, and Western Blot Analysis

An anti-peptide rabbit polyclonal antibody was made to a peptide, (C)AGQKEKDEALEEKLRN (SEQ ID NO: 8) (Quality Controlled Biochemicals, Hopkinton Mass.), which corresponded to DGKι residues $A^{109}$–$N^{124}$. The N-terminal cysteine residue was used to couple the peptide to a carrier protein (keyhole limpet hemocyanin) prior to immunization. The antibody was affinity purified from serum using the same peptide.

Transfected COS-7 cells were harvested and separated into cytoplasmic and nuclear fractions as described in B. Payraxtre et al. (1992), *J. Biol. Chem.* 267:5078–5084. Samples from whole transfected COS-7 cells and from the cytoplasmic and nuclear fractions of such cells were loaded on a 7.5% SDS-PAGE gel. Following electrophoresis, the proteins were transferred to the Millipore membrane. For the peptide competition experiment, the primary antibody was incubated with 4 volumes of 100 ng/ml peptide at 4° C. for 2 h prior to incubation with the membrane. Western blot was performed as described in Bunting et al.

Example 7

Isolation of a Genomic Clone and Chromosomal Localization

DGKι cDNA was purified and used to isolate a genomic clone from a human Bac library (Genome System Inc). Fluorescence in situ hybridization was performed as described in D. Pinkel et al. (1986), *Proc. Natl. Acad. Sci. U.S.A.* 83:2934–2938.

Summary

In summary, the present invention relates to a novel human DGK isoform, DGKι. The present invention provides nucleic acid molecules that encode such DGK molecules. The present invention also provides recombinant vectors comprising such nucleic acid molecules. The present invention further provides host cells comprising a nucleic acid that codes for DGKι. Further embodiments of the present invention include in vitro methods of using nucleic acids coding for DGKs to decrease intracellular levels of DAG and increase intracellular levels of phosphatidic acid.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. An isolated and purified nucleic acid, said nucleic acid comprising nucleotides which code for the amino acid sequence of SEQ ID NO: 2.

2. An isolated and purified nucleic acid which codes for human diacylglycerol kinase ι, said nucleic acid comprising the nucleotide sequence of SEQ ID NO: 1.

3. A recombinant vector comprising the nucleic acid molecule of claim 2.

4. The recombinant vector of claim 3, wherein said recombinant vector is a plasmid.

5. The recombinant vector of claim 3, wherein said recombinant vector is a prokaryotic or eukaryotic expression vector.

6. The recombinant vector of claim 3, wherein the nucleic acid molecule is operably linked to a heterologous promoter.

7. A host cell comprising the nucleic acid of claim 2.

8. The host cell of claim 7, wherein the host cell is a eukaryotic host cell.

9. The host cell of claim 7, wherein the host cell is a prokaryotic host cell.

10. An in vitro method of decreasing intracellular levels of diacylglycerol and increasing intracellular levels of phosphatidic acid comprising introducing into a eukaryotic cell a nucleic acid, said nucleic acid comprising the nucleotide sequence of SEQ ID NO: 1.

11. An isolated and purified nucleic acid sequence whose complement hybridizes to SEQ ID NO: 1 under the conditions of 65° C. overnight in a solution comprising 5×SSPE, 5×Denhardt's, 0.2% SDS, and 0.1% $Na_2P_4O_7$, followed by washing twice in 0.6×SSPE, 0.1% SDS, and 0.1% $Na_2P_4O_7$ at 65° C. for 30 minutes, wherein said nucleic acid sequence codes for a protein having diacylglycerol kinase enzymatic activity.

12. The nucleic acid sequence defined in claim 11, wherein said nucleic acid sequence is subcloned into a plasmid.

13. The nucleic acid sequence defined in claim 11, wherein said nucleic acid sequence is subcloned into a prokaryotic or eukaryotic expression vector.

14. The nucleic acid sequence defined in claim 11, wherein said nucleic acid sequence is stably or transiently incorporated into a prokaryotic or eukaryotic host cell.

15. An in vitro method of decreasing intracellular levels of diacylglycerol and increasing intracellular levels of phosphatidic acid comprising introducing into a eukaryotic cell the nucleic acid sequence of claim 11.

* * * * *